(12) United States Patent
Bloomfield et al.

(10) Patent No.: US 10,711,021 B2
(45) Date of Patent: Jul. 14, 2020

(54) METAL OXIDE-ORGANIC HYBRID MATERIALS FOR HETEROGENEOUS CATALYSIS AND METHODS OF MAKING AND USING THEREOF

(71) Applicant: Yale University, New Haven, CT (US)

(72) Inventors: Aaron J. Bloomfield, New Haven, CT (US); Stafford W. Sheehan, Tiverton, RI (US); Samuel L. Collom, New Haven, CT (US); Robert H. Crabtree, Bethany, CT (US); Paul T. Anastas, Guilford, CT (US)

(73) Assignee: YALE UNIVERSITY, New Haven, CT (US)

( * ) Notice: Subject to any disclaimer, the term of this patent is extended or adjusted under 35 U.S.C. 154(b) by 478 days.

(21) Appl. No.: 14/950,791

(22) Filed: Nov. 24, 2015

(65) Prior Publication Data

US 2016/0152648 A1 Jun. 2, 2016

Related U.S. Application Data

(62) Division of application No. 14/322,773, filed on Jul. 2, 2014.

(Continued)

(51) Int. Cl.

| | | |
|---|---|---|
| C07F 15/06 | (2006.01) | |
| C07C 45/28 | (2006.01) | |
| C07C 29/48 | (2006.01) | |
| C07D 307/20 | (2006.01) | |
| C07C 51/16 | (2006.01) | |
| C07C 45/27 | (2006.01) | |
| C07D 207/12 | (2006.01) | |
| C07B 33/00 | (2006.01) | |
| C02F 1/467 | (2006.01) | |
| H01M 4/90 | (2006.01) | |
| G01N 27/407 | (2006.01) | |
| C02F 1/72 | (2006.01) | |
| B01J 31/22 | (2006.01) | |
| B01J 31/24 | (2006.01) | |
| C25B 11/04 | (2006.01) | |
| C25C 1/00 | (2006.01) | |
| C25C 1/16 | (2006.01) | |
| C25B 1/04 | (2006.01) | |

(Continued)

(52) U.S. Cl.
CPC ........... *C07F 15/06* (2013.01); *B01J 31/2273* (2013.01); *B01J 31/2278* (2013.01); *B01J 31/2409* (2013.01); *B01J 35/004* (2013.01); *C02F 1/4678* (2013.01); *C02F 1/725* (2013.01); *C07B 33/00* (2013.01); *C07C 29/48* (2013.01); *C07C 45/27* (2013.01); *C07C 45/28* (2013.01); *C07C 51/16* (2013.01); *C07D 207/12* (2013.01); *C07D 307/20* (2013.01); *C07F 11/00* (2013.01); *C07F 13/00* (2013.01); *C07F 15/0033* (2013.01); *C07F 15/0073* (2013.01); *C07F 15/02* (2013.01); *C07F 15/04* (2013.01); *C25B 1/04* (2013.01); *C25B 3/02* (2013.01); *C25B 3/04* (2013.01); *C25B 11/0442* (2013.01); *C25C 1/00* (2013.01); *C25C 1/16* (2013.01); *G01N 27/4075* (2013.01); *H01M 4/9016* (2013.01); *B01J 2231/62* (2013.01); *B01J 2231/70* (2013.01); *B01J 2531/845* (2013.01); *B01J 2531/847* (2013.01); *C02F 1/4672* (2013.01); *C02F 2001/46142* (2013.01); *C02F 2101/308* (2013.01); *C02F 2101/366* (2013.01); *Y02E 60/366* (2013.01)

(58) Field of Classification Search
None
See application file for complete search history.

(56) References Cited

U.S. PATENT DOCUMENTS

| | | |
|---|---|---|
| 3,897,328 A | 7/1975 | Mitchell |
| 2008/0248195 A1 | 10/2008 | Reetz |

(Continued)

FOREIGN PATENT DOCUMENTS

| | | |
|---|---|---|
| CA | 2755820 | 12/2009 |
| EP | 0987054 | 6/2004 |

(Continued)

OTHER PUBLICATIONS

Travis et al. Eur. J. org. Chem., 3429-3434 (Year: 2002).*

(Continued)

*Primary Examiner* — Yun Qian
(74) *Attorney, Agent, or Firm* — Pabst Patent Group LLP

(57) ABSTRACT

Catalysts prepared from abundant, cost effective metals, such as cobalt, nickel, chromium, manganese, iron, and copper, and containing one or more neutrally charged ligands (e.g., monodentate, bidentate, and/or polydentate ligands) and methods of making and using thereof are described herein. Exemplary ligands include, but are not limited to, phosphine ligands, nitrogen-based ligands, sulfur-based ligands, and/or arsenic-based ligands. In some embodiments, the catalyst is a cobalt-based catalyst or a nickel-based catalyst. The catalysts described herein are stable and active at neutral pH and in a wide range of buffers that are both weak and strong proton acceptors. While its activity is slightly lower than state of the art cobalt-based water oxidation catalysts under some conditions, it is capable of sustaining electrolysis at high applied potentials without a significant degradation in catalytic current. This enhanced robustness gives it an advantage in industrial and large-scale water electrolysis schemes.

30 Claims, 12 Drawing Sheets

Related U.S. Application Data

(60) Provisional application No. 61/842,621, filed on Jul. 3, 2013.

(51) Int. Cl.

| | |
|---|---|
| *C25B 3/02* | (2006.01) |
| *C25B 3/04* | (2006.01) |
| *B01J 35/00* | (2006.01) |
| *C07F 11/00* | (2006.01) |
| *C07F 13/00* | (2006.01) |
| *C07F 15/00* | (2006.01) |
| *C07F 15/02* | (2006.01) |
| *C07F 15/04* | (2006.01) |
| *C02F 1/461* | (2006.01) |
| *C02F 101/30* | (2006.01) |
| *C02F 101/36* | (2006.01) |

(56) References Cited

U.S. PATENT DOCUMENTS

| | | |
|---|---|---|
| 2012/0214084 A1 | 8/2012 | Sharman |
| 2013/0037417 A1 | 2/2013 | Jia |
| 2014/0054180 A1 | 2/2014 | Morimitsu |

FOREIGN PATENT DOCUMENTS

| | | |
|---|---|---|
| EP | 1701790 | 9/2009 |
| WO | 2009029539 | 3/2009 |
| WO | 2009154753 | 12/2009 |
| WO | 2012122605 | 9/2012 |
| WO | 2013100162 | 7/2013 |

OTHER PUBLICATIONS

Yu et al. (Organometallics, 2009, 28, 4443-4451). (Year: 2009).*
Shul'pin et al. (Tetrahedron Letter, 2005, 46, 4563-4567). (Year: 2005).*
Spirina et al., Zhuurnal Obshchei Khimii/Zh. Obshch. Khim., 62(12), 1992, 2656-2662 (Year: 1992).*
Spirina et al. (Zhuurnal Obshchei Khimii/Zh. Obshch. Khim., 62(12), 1992, 2656-2662, Abstract and Reaction Scheme cited from SciFinder). (Year: 1992).*
Carter, et al., "Oxygen carrier and redox properties of some natural cobalt chelates. Axial and in-plane ligand effects" J Am Chem Soc., 96:2 (1974).
Casadesus, et al., "A oxygen-dependent reductive dechlorination of chloroform by (Bisdiphenylphosphinomethane)cobalthexacarbonyl Co2(CO)6(dppm)" J Organometalic Chem., 691:3715-7 (2008).
Du, et al., "Elucidating the domain structure of the cobalt oxide water splitting catalyst by X-ray pair distribution function analysis", J Am Chem Soc., 134(27):11096-9 (2012).
Hanson, et al., "Reactions of the linked cobalt dimer Co2(CO)6(Ph2PCH2PPh2). Molecular structure of (.mu.-H)(.mu.-PPh2)Co2(CO)4(Ph2PCH2PPh2)", Inorganic Chem., 21(10):3811-5 (1982).
Invine, et al., "Transition metal-boryl compounds ; Synthesis, reactivity and structure", Chem Rev., 98:2585-722 (1998).
Rigo, et al., "Reactions of dicyanodi-[1,2-bis(diphenylphosphino)ethane]cobalt(II) with oxygen and alkyl halides", J Chem Soc. D,10:598a (1970).
Weber, et al., "Hydroformylation of epoxides catalyzed by cobalt and hemilabile P-O ligands", Chem Comm., 15:1419-20 (2000).
Aime, et al., "The reaction of Co4(CO)12 with Ph2PCH2CH2PPh2. Spectroscopic identification of polymeric products", J Organomet Chem., 309:C51 (1986).
Ayers, "An overview of electrochemical carbon dioxide reduction", Spec Publ—R Soc Chem., 153:365-74 (1994).
Ayres and Peiro, "Material efficiency: rare and critical metals", Philos Trans R Soc A., 371:20110563 (2013).
Blakemore, et al., "Anodic Deposition of a Robust Iridium Water-Oxidation Catalyst from Organometallic Precursors", Chem Sci., 2:94-8 (2011).
Bloomfield, et al., "A heterogeneous water oxidation catalyst from dicobalt octacarbonyl and 1,2-bis(diphenylphospino)ethane", New J Chem., 38:1540-5 (2014).
Bockris and Otagawa, "The Electrocatalysis of Oxygen Evolution on Perovskites", J Electrochem. Soc., 131:290-302 (1984).
Cunninghame, et al., "Electron transfer in organometallic clusters. 12. Regioselective sequential electrocatalytic substitution of [.mu.-(CF3)2C2]Co2(CO)6 by polydentate ligands", Organometallics, 6:1470-9 (1987).
Dinca, et al., "Nickel-borate oxygen-evolving catalyst that functions under benign conditions", PNAS, 107:10337-41 (2010).
Erdmann and Graedel, "Criticality of non-fuel minerals: a review of major approaches and analyses", Environ Sci Technol, 45:7620-30 (2011).
Esswein, et al., "Highly active cobalt phosphate and borate based oxygen evolving catalysts operating in neutral and natural waters", Energy Environ., 4:499- (2011).
Gutowski, et al., "The energy required to produce materials: constraints on energy-intensity improvements, parameters of demand", Philos Trans R Soc A., 371:2012003 (2013).
Hintermair, et al., "Precursor transformation during molecular oxidation catalysis with organometallic iridium complexes", J Am Chem Soc., 135:10837-51 (2013).
Irshad and Munichandraiah, "EQCM Investigation of Electrochemical Deposition and Stability of Co—Pi Oxygen Evolution Catalyst of Solar Energy Storage", J Phys Chem C., 117:8001-8 (2013).
Ismail and Badawy, "Electrochemical and XPS investigations of cobalt in KOH solutions", J Appl. Electrochem., 30:1303-11 (2000).
Iwakura, et al., "The anodic evolution of oxygen on Co3O4 film electrodes in alkaline solutions", Electrochim Acta, 26:1319-26 (1961).
Jitaru, et al., "Electrochemical reduction of carbon dioxide on flat metallic cathodes", J Appl Electrochem., 27:876-89 (1997).
Kanan and Nocera, "In situ formation of an oxygen-evolving catalyst in neutral water containing phosphate and Co2+. ", Science 321:1072-5 (2008).
Kanan, et al., "Structure and valency of a cobalt-phosphate water oxidation catalyst determined by in situ X-ray spectroscopy", J Am Chem Soc., 132:13692-710 (2010).
King, et al., "Kinetics of Nucleation, Growth and Stabilization of Cobalt Oxide Nanoclusters", J Phys Chem B., 107:12097-104 (2003).
Lewis and Nocera, "Powering the planet: chemical challenges in solar energy utilization", PNAS, 103:15729-35 (2006).
Lutterman, et al., "A self-healing oxygen-evolving catalyst", J Am Chem Soc., 131:3838-9 (2009).
Merrill and Dougherty, "Metal Oxide Catalysts for the Evolution of O2 from H2O", J Phys Chem C, 112:3655-66 (2008).
Meyer, "Chemical approaches to artificial photosynthesis", Acc Chem Res., 22:163-70 (1989).
Miles, et al., "The Oxygen Electrode Reaction in Alkaline Solutions on Oxide Electrodes Prepared by the Thermal Decomposition Method", J Electrochem Soc., 125:1931-4 (1978).
Nocera, "The artificial leaf", Acc Chem Res, 45:767-76 (2012).
Pintado, et al., "Fast and persistent electrocatalytic water oxidation by Co—Fe Prussian blue coordination polymers", J Am Chem. Soc., 135:13270-3 (2013).
Seley, et al., "Combinatorial search for improved metal oxide oxygen evolution electrocatalysts in acidic electrolytes", ACS Comb Sci, 15:82-9 (2013).
Smith, et al., "Photochemical route for accessing amorphous metal oxide materials for water oxidation catalysis", Science, 340:60-3 (2013).
Surendranath, et al., "Electrolyte-dependent electrosynthesis and activity of cobalt-based water oxidation catalysts", J Am Chem Soc., 131:2615-20 (2009).
Surendranath, et al., "Nucleation, growth, and repair of a cobalt-based oxygen evolving catalyst", J Am Chem Soc., 134:6326-36 (2012).

(56) References Cited

OTHER PUBLICATIONS

Tang, et al., "Characterization of Cobalt Oxides Studied by FT-IR, Raman, TPR and TG-MS", Thermochin Acta, 473:68-73 (2008).
Thomsen, et al., "Electrochemical activation of Cp* Iridium complexes for electrode-driven water-oxidation catalysis", J Am Chem Soc., 136:13826-34 (2014).
Yagi, et al., "Self-assembly of active IrO2 colloid catalyst on an ITO electrode for efficient electrochemical water oxidation", J Phys Chem B., 109:21489-91 (2005).
Zaharieva, et al., "Electrosynthesis, functional, and structural characterization of a water-oxidizing manganese oxide", Energy Environ Sci., 5:7081-9 (2012).
Zhang and Ren, "Silica supported ruthenium oxide nanoparticulates as efficient catalysts for water oxidation", Chem Commun., 48:11005 (2012).
Bae, et al., "Effects of Surface Anchoring Groups (Carboxylate vs Phosphonate) in Ruthenium-Complex-Sensitized TiO2 on Visible Light Reactvity in Aqueous Suspensions", Journal of Physical Chemistry B, 108:14093-14101 (2004).
Morvillo, et al., "Prepaeration and reactivity of new dioxygen adducts of rhodium containing phosphine ligands", Inorganica Chimica Acta, 121(1):219-222 (1986).
Reinaud, et al., "Novel Binuclear Cobalt Dioxygen Complex—A Step on the Path to Dioxygen Activation", Chemie International Edition, 34(18):2051-2052 (2003).
Zhao, et al., "Immobilizing catalysts on porous materials", Materials Today 9(3):32-39 (2006).

* cited by examiner

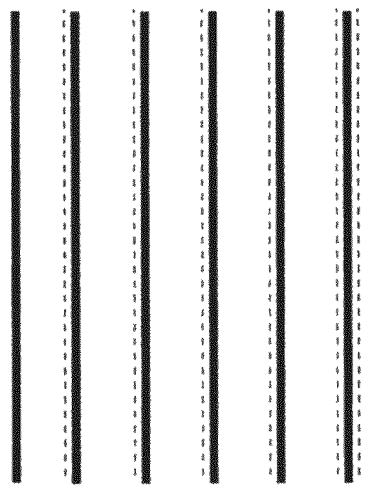
Fig. 16
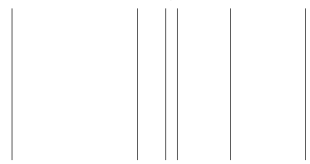

METAL OXIDE-ORGANIC HYBRID MATERIALS FOR HETEROGENEOUS CATALYSIS AND METHODS OF MAKING AND USING THEREOF

CROSS-REFERENCE TO RELATED APPLICATIONS

This application claims the benefit of and priority to U.S. Ser. No. 61/842,621 filed Jul. 3, 2013 and which is incorporated by reference in its entirety.

STATEMENT REGARDING FEDERALLY SPONSORED RESEARCH OR DEVELOPMENT

This invention was made with government support under Agreement Nos. 1122492 and 1119826 awarded by the National Science Foundation, and support under Agreement No. DE-FG02-84ER13297 awarded by the Department of Energy. The Government has certain rights in the invention.

FIELD OF THE INVENTION

This invention is in the field of catalysis, particularly for applications in water-oxidation, oxidation of organic species, oxygen reduction, and/or reducing metal ions and/or other species, such as organic species.

BACKGROUND OF THE INVENTION

The electrochemical production of oxygen from water has been studied extensively as a component of water-splitting schemes which can be used in the sustainable generation of hydrogen by electrolysis of water and a renewable energy source, such as sunlight. The water oxidation half-reaction may also serve as the anodic half reaction coupled with other aqueous electrochemical reductions, such as electrodeposition of metals and/or organic electroreductions. In these schemes, higher efficiency of water oxidation afforded by a catalyst reduces the overall amount of energy needed for these processes. Although some oxides and organometallic compounds of 2nd and 3rd row transition metals, such as Ru, Rh, Ir, and Pt are among the most active water oxidation catalysts known, their low abundance and the high cost of such metals are substantial obstacles to their widespread application.

Cobalt oxides and the recently developed cobalt phosphate/phosphonate/borate compounds (e.g., Co-Pi) offer significantly more affordable and scalable alternatives. These cobalt catalysts are not without their drawbacks, however. Their primary method of synthesis is through electrodeposition. These catalysts are prone to degradation at the high currents required for commercial water electrolysis, as well as in buffers that do not contain a significant concentration of phosphate, or other strong proton acceptor.

There exists a need for catalysts that do not suffer from the limitations described above.

Therefore, it is an object of the invention to provide catalysts, particularly oxidation catalysts, that do not suffer from the limitations described above and methods of making and using thereof.

SUMMARY OF THE INVENTION

Catalysts prepared from d-block transition metals and containing one or more charged and/or uncharged ligands (e.g., monodentate, bidentate, and/or polydentate ligands) and methods of making and using thereof are described herein. In some embodiments, the d-block transition metal is one that forms stable carbonyl complexes. Exemplary metals include, but are not limited to, cobalt (Co), nickel (Ni), chromium (Cr), manganese (Mn), iron (Fe), copper (Cu), Rhodium (Rh), and/or Iridium (Ir). Exemplary ligands include, but are not limited to, phosphine ligands, nitrogen-based ligands (e.g., diamines, N-containing heterocycles), sulfur-based ligands, and/or arsenic-based ligands. In some embodiments, the catalyst is a cobalt-based catalyst, nickel-based catalyst, rhodium-based catalyst, or iridium-based catalyst.

The catalysts described herein are stable to a maximum overpotential of at least about 500, 550, 600, 650, 700, 750, 780, or 800 My at neutral pH or at least about 500, 550, 600, 650, 700, 750, 780, 800, 900, 1000, 1100, or 1200 mV at alkaline pH. For example, the catalysts described herein were subjected to a potential 300 mV higher than the limit reported for Nocera's catalyst. No change in the catalyst/catalytic activity over 40 hours; little or no Co and/or P was found in the electrolyte solution when assayed using ICP-MS. The catalysts can be used in any of the commonly used electrolyte systems, such as borate, phosphate buffers, hydroxide, nitrate, and/or sulfate.

The catalysts described herein are stable and active at neutral pH, in a wide range of buffers that are both weak and strong proton acceptors, and at highly basic pH, e.g., greater than 10, such as pH 13 to 30 wt % KOH, and in the presence of high concentrations of soluble metal ions, such as $Zn^{2+}$. The examples show that catalysts are stable at strongly alkaline pH for a period of at least 20, 30, 40, 50, 60, 70, 80, 90, 100 days or greater.

While the activity of the cobalt-based catalyst described herein is slightly lower than state of the art cobalt-based water oxidation catalysts under some conditions, the cobalt-based catalyst is capable of sustaining electrolysis at high applied potentials without a significant degradation in catalytic current. This enhanced robustness gives it an advantage in industrial and large-scale water electrolysis schemes.

The catalysts described herein can be incorporated into the oxygen-producing anode of a variety of devices for purposes including, but not limited to, splitting water by electrolysis to produce hydrogen at the cathode, splitting water by electrolysis to produce oxygen at the anode, reducing metal ions to their corresponding metallic neutral state at the cathode, reduction of organic species by electrolysis at the cathode, reduction of any other species at the cathode, as long as it is coupled with oxygen production at the anode, and combinations thereof. These electrolytic processes can be driven by a variety of energy sources, such as solar, wind, and/or nuclear.

Being potent enough to oxidize water, these catalysts are also capable of oxidizing a wide range of organic compounds with applications toward oxidative synthesis of specialized chemicals, as well as degradation of harmful organic species.

The catalysts described herein can also be incorporated into the oxygen-consuming cathode of a variety of devices including, but not limited to, oxygen-scavenging devices, oxygen-detectors, and fuel cells or batteries which consume oxygen (pure, or in mixtures, such as air, or specialty gas mixtures) in addition to any fuel including, but not limited to, hydrogen, organic fuels, metallic fuels, or inorganic fuels.

BRIEF DESCRIPTION OF THE DRAWINGS

FIG. 10M is a control without catalyst.

FIG. 16 is an illustration of a dry-cell alkaline electrolyzer used in Example 5 (solid lines represent electrodes and dashed lines present catalyst coating).

DETAILED DESCRIPTION OF THE INVENTION

I. Definitions

Figure 1:
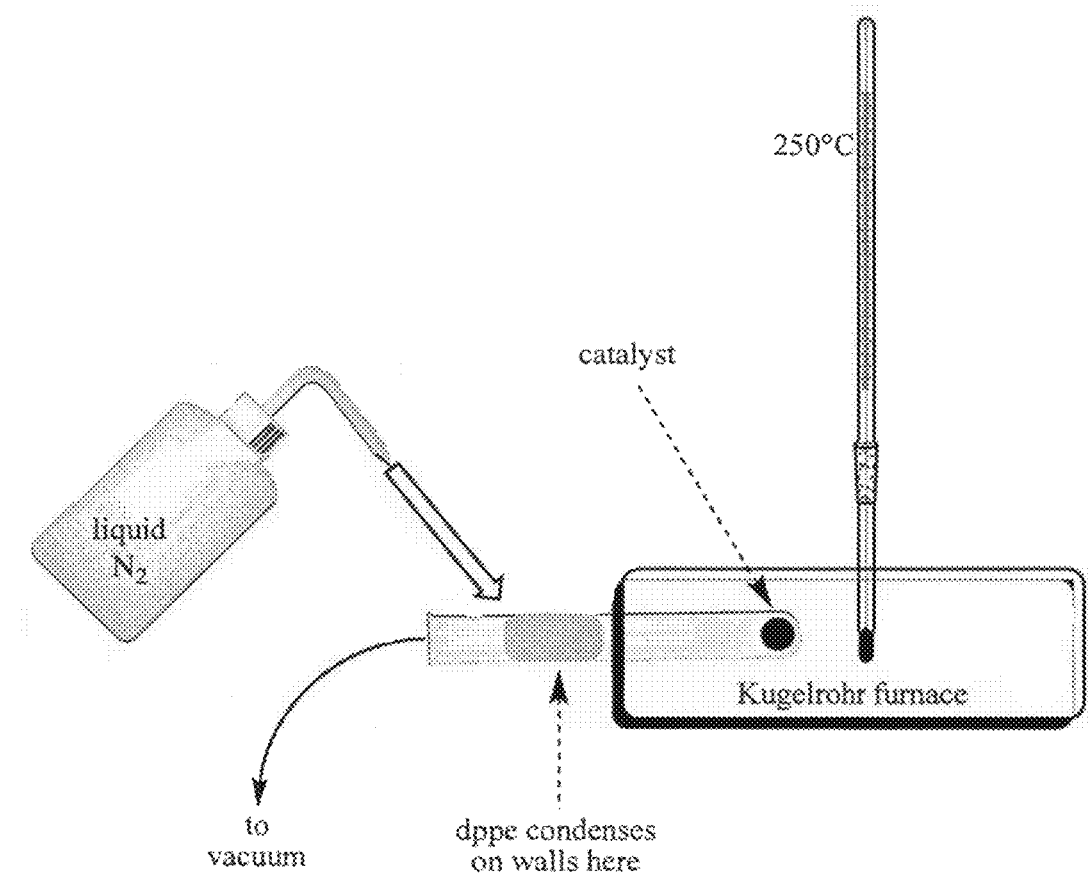
FIG. 1 is a schematic of the apparatus used for destructive distillation.

"Water oxidation catalyst", "WOC", "oxygen evolving catalyst", and "OEC" are used interchangeably and refer to a catalyst used to oxidize water to form oxygen ($O_2$) and hydrogen ($H^+$) ions. Oxygen yield can be monitored using a variety of techniques. In one embodiment, oxygen yield is monitored using phase-shift fluorescence detection.

"Heterogeneous", as used herein, refers to the form of catalysis where the phase of the catalyst differs from that of the reactants "Homogeneous", as used herein, means the catalyst is soluble (i.e., same phase as the reactants) in the reaction solution.

"Oxidatively stable" as used herein, means that more than 90%, more than 92%, more than 94%, more than 95%, more than 98%, more than 99%, more than 99.5%, more than 99.9%, more than 99.95%, more than 99.99% of the catalyst is structurally intact in the presence of one or more oxidants including, but not limited to, $O_2$, $O_3$, and peroxides, at a high applied potential (0.5-3.0 V vs Ag/AgCl) over a broad pH range (e.g., 6-16) for at least 7 days, 14 days, 21, days, 28 days, 30 days, 45 days, two months, three months, four months, five months, six months, one year, or longer at ambient temperature and ambient light conditions. Alternatively, the catalyst undergoes less than 10%, less than 5%, less than 1%, less than 0.5%, less than 0.1%, less than 0.05%, or less than 0.01% oxidation under the conditions described above "Hydrolytically stable", as used herein, means that more than 90%, more than 92%, more than 94%, more than 95%, more than 98%, more than 99%, more than 99.5%, more than 99.9%, more than 99.95%, more than 99.99% of the catalyst is structurally intact in the presence of water over a broad pH range (e.g., 6-16) for at least 7 days, 14 days, 21, days, 28 days, 30 days, 45 days, two months, three months, four months, five months, six months, one year, or longer at ambient temperature and ambient light conditions. Alternatively, the catalyst undergoes less than 10%, less than 5%, less than 1%, less than 0.5%, less than 0.1%, less than 0.05%, or less than 0.01% hydrolysis under the conditions described above. In a particular embodiment, the catalyst undergoes no structural changes under the conditions described above.

"Thermally stable", as used herein, means that more than 90%, more than 92%, more than 94%, more than 95%, more than 98%, more than 99%, more than 99.5%, more than 99.9%, more than 99.95%, more than 99.99% of the catalyst is structurally intact at room temperature or lower or when heated to a temperature above room temperature. In a particular embodiment, the catalyst undergoes no structural changes when heated above room temperature.

"Turn over number" or "TON", as used herein, means the number of moles of substrate that a mole of catalyst can convert before being inactivated. TON is calculated as the number of moles of oxygen, $n_{O2}$, divided by the number of moles of catalyst, $n_{cat}$.

"Turn over frequency" or "TOF", as used herein, refers to the turnover per unit time under turnover conditions. It is typically expressed in $s^{-1}$. The TOF can be calculated by dividing the TON by the time period, in seconds, over which the TON was measured.

"Turnover conditions", as used herein, refers to the conditions in which the catalytic reaction takes place. "Turnover conditions" include at a minimum pH and temperature. Other criteria include concentration of the oxidant and concentration of the WOC. The turnover conditions can vary for a given WOC.

"Oxygen yield", as used herein, refers to the percent oxygen formed during the catalytic reaction. It is expressed as a percent by weight of an oxidant or sacrificial electron acceptor.

"Oxidant" or "sacrificial electron acceptor", as used herein, refers to the molecule that is reduced during the oxidation of water.

"Light collecting molecule", as used herein, refers to the molecule in the catalytic system that absorbs light creating a charge separated excited state.

"Hydrogen reduction catalyst" and "hydrogen evolving catalyst" are used interchangeably and refer to a catalyst which reduce protons to form hydrogen gas.

"Alkyl", as used herein, refers to the radical of saturated or unsaturated aliphatic groups, including straight-chain alkyl, heteroalkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. In some embodiments, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. Likewise, preferred cycloalkyls have from 3-10 carbon atoms in their ring structure, and more preferably have 5, 6 or 7 carbons in the ring structure. The ranges provided above are inclusive of all values between the minimum value and the maximum value.

The term "alkyl" includes "heteroalkyls", "unsubstituted alkyls", and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

The alkyl groups may also contain one or more heteroatoms within the carbon backbone. Preferably the heteroatoms incorporated into the carbon backbone are oxygen, nitrogen, sulfur, and combinations thereof. In certain embodiments, the alkyl group contains between one and four heteroatoms.

"Alkenyl" and "Alkynyl", as used herein, refer to unsaturated aliphatic groups containing one or more double or triple bonds analogous in length (e.g., $C_2$-$C_{30}$) and possible substitution to the alkyl groups described above.

"Aryl", as used herein, refers to 5-, 6- and 7-membered aromatic ring. The ring may be a carbocyclic, heterocyclic, fused carbocyclic, fused heterocyclic, bicarbocyclic, or biheterocyclic ring system, optionally substituted by halogens, alkyl-, alkenyl-, and alkynyl-groups. Broadly defined, "Ar", as used herein, includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl", "aryl heterocycles", or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro [2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, ($C_{1-4}$) alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms consisting of carbon and 1, 2, 3, or 4 heteroatoms each selected from the group consisting of non-peroxide oxygen, sulfur, and N(Y) where Y is absent or is H, O, ($C_1$-$C_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

"Halogen", as used herein, refers to fluorine, chlorine, bromine, or iodine.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

II. Catalysts

Catalysts that exhibit several differences from previously identified oxide materials are described herein. The catalysts show improved stability at high overvoltages (600-800 mV), with weakly basic electrolytes ($SO_4^{2-}$ and $NO_3^-$), and overvoltages up to or greater than 1200 mV in strongly basic conditions, e.g., greater than pH 10, such as pH 12 to 30 wt % KOH.

In some embodiments, the catalyst has the formula:

$$MY_a(CO)_bO_c(OH)_d(H_2O)_e$$

wherein
M is a d-block transition metal, preferably one that forms stable carbonyl complexes;
Y is a monodentate ligand, bidentate ligand, polydentate ligand, or combination thereof;
a is any value from 0-3, preferably 0.5-1;
b is any value from 0-3, preferably 0-2;
c is any value from 1-4, preferably 1.5-3;
d is any value from 0-4; and
e is any value from 0-6.

In some embodiments, M includes, but is not limited to, Cr, Mn, Fe, Co, Ni, Cu, Rh, Ir, or combinations thereof In some embodiments, M is Co and/or Ni.

In some embodiments, M is Co and/or Ni and the preferred values for a-e are as described above.

In some embodiments, the ligands are not charged, i.e., have no charged atoms. The use of neutral ligands to prepare metal oxide-based heterogeneous catalysts is generally not found in the art. In some embodiments, the ligands are charged, wherein the charge resides on an atom or atoms that does participate in a bond or coordination with the metal. In contrast, the ligands in most prior art catalyst systems, such as Nocera's catalyst, are charged at the site of interaction with the metal, likely to enhance solubility to facilitate synthesis.

In some embodiments, M and a-e are as defined above, and Y is a phosphorus-based ligand. In particular embodiments, the phosphorus-based ligand is selected from P-heterocycles, or primary, secondary or tertiary phosphines with alkyl, aryl or heteroatom substituents, primary, secondary, or tertiary phosphine oxides with alkyl, aryl, or heteroatom substituents, or any combination thereof. In more particular embodiments, the ligand is an alkyl diaryl phosphine or a triayl phosphine. Exemplary alkyldiaryl phosphines include, but are not limited to, dppe. Exemplary triaryl phosphines include, but are not limited to Xantphos, triphenylphosphine, DPEphos, 1,2-ethanediylbis[diphenylphosphine oxide], 1,1-Bis(diphenylphosphino)methane (dppm), 1,1-Bis(diphenylphosphino)ethane (dppe), 1,1-Bis(diphenylphosphino)propane (dppp), 1,1-Bis(diphenylphosphino)butane (dppb), and combinations thereof.

The selection of phosphine ligands is counterintuitive as such ligands are notoriously susceptible to oxidation (to P=O) or other types of degradation under the conditions used to prepare the catalysts described herein. However, no such oxidation or degradation was observed during or after synthesis. In some embodiments, during working conditions, partial degradation of the ligand is observed. In other embodiments, during working conditions, complete degradation of the ligand is observed; however the structural integrity and activity of the nanoparticle is retained.

ICP-MS data show that for cobalt-phosphine-based catalysts, the P:Co atomic ratio is typically between 1:1 and 1:2. The phosphine ligand may help stabilize the particles and inhibit Co leaching typically seen in prior art cobalt-based catalysts. By incorporating an organic phosphine unit, the solubility of the material in water is minimized, increasing the stability of the material under aqueous conditions. This property may result from the water-insolubility of the phosphine unit. This increased stability allows for use of cheaper electrolytes and higher currents.

In other embodiments, M and a-e are as defined above and the bidentate ligand is a nitrogen-based ligand, a sulfur-based ligand, an arsenic-based ligand, any combination thereof, or any combination with a phosphine. In particular embodiments, the nitrogen-based ligand is selected from N-heterocycles, or primary, secondary or tertiary amines, with alkyl and/or aryl substituents; the sulfur-based ligand is selected from S-heterocycles, or alkyl and/or aryl thioethers; the arsenic-based ligand is selected from As-heterocycles or any tertiary arsine with alkyl and/or aryl substituents. Exemplary nitrogen-based ligands include, but are not limited to, 1,2-Bis(1-piperidinyl)ethane, TMEDA, EDTA, 2,2'-bipyridine, and combinations thereof.

The ligands can contain one or more alkyl and/or aryl groups as defined above. The alkyl and/or aryl groups can be substituted or unsubstituted. Suitable substituents are known in the art and include, but are not limited to, halogens, hydroxyl groups, nitro, alkyl, substituted alkyl, alkenyl, substituted alkenyl, alkynyl, substituted alkynyl, phenyl, substituted phenyl, aryl, substituted aryl, heteroaryl, substituted heteroaryl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, and substituted heterocyclic groups.

A. Heterogeneous Catalysts

The catalysts described herein can be used as heterogeneous catalysts. The catalysts can be readily applied as coating or layer to a substrate, such as the surface of an electrode. The coating or layer can be cast from suspension, and do not require an external stimulus (e.g., current (electrochemical) or heat) for layer formation. In some embodiments, the surface is densely or sparsely studded with particles of catalyst. The necessary loading is low enough that a fully coated electrode is still completely transparent, which is beneficial for use in photovoltaic or photochemical cells.

The catalysts described herein can be coated on a variety of substrates including, but not limited to, conductive substrates, photocatalytic substrates, and combinations thereof. Exemplary substrates include, but are not limited to, oxides, such as tin-doped indium oxide (ITO), fluorine doped tin oxide (FTO), tin oxide ($SnO_2$), tungsten oxide ($WO_3$), iron oxide ($Fe_2O_3$), and titanium dioxide ($TiO_2$); carbon-based electrodes (typically used in fuel cells), such as glassy carbon, wooly carbon, and conductive carbon fiber; and metals, such as aluminum, copper, iron, lead, nickel, silver, stainless steel, titanium, and zinc, or any alloys containing these metals. Many of these metals oxidize easily, so it is possible the catalyst adheres to an oxide layer on the metal surface and not the metal itself.

The catalysts described herein are likely nanomaterials (e.g., nanoparticles) rather than molecular catalysts. The average diameter of the particles can vary. However, in some embodiments, the average diameter is from about 1 to 500 nm, preferably from about 5 to about 400 nm, more preferably from about 5 to about 300 nm, more preferably from about 10 nm to about 300 nm, most preferably from about 15 nm to about 300 nm. In some embodiments, the catalyst is largely amorphous as measured by HRTEM and XRD.

In some embodiments, the nanomaterial contains a core unit containing a plurality of metal (e.g., cobalt) atoms. In some embodiments, the number of metal atoms is from about 2 to about 20, preferably from about 4 to about 16. The metal atoms are surrounded by oxygen atoms, possibly in a cubane structure. The cubane structure can be decorated and/or interconnected by the phosphine ligands and/or other types of ligands.

In some embodiments, upon coating onto a substrate, a substantial amount of the catalyst detaches from the surface leaving roughly 15-20% of the substrate surface coated with the catalyst. However, even at these relatively sparsely-coated areas, the catalysts described herein exhibit significantly higher activity per mass of cobalt than Nocera's family of Co-Xi catalysts (where Xi is an inorganic oxyanion; X=P, MeP, B, etc.), which are deposited as a film electrochemically and necessarily thoroughly coat the electrode surface. The fact that less materials can be used to achieved the same or better performance than the prior art catalysts should result in lower cost which is important for larger scale commercial applications.

The catalysts described herein are stable over a broad pH range, such as about 4.0 to over 14 or 30 wt % KOH, preferably from about 6.0 to about 10, more preferably from about 4.5 to about 9.5. The catalysts described herein are also active for prolonged periods in unadulterated sea water or preferably sea water containing additives, such as borate or hydroxide. The additives increase the ionic strength (decrease electric resistance of the electrolyte) and/or improve the proton-accepting capability of the electrolyte. Some prior art catalysts, such as Nocera's, require addition of phosphate or borate to naturally sourced waters, to avoid catalyst deactivation. Other prior art catalysts require the addition of strong acids or bases to perform water oxidation.

The catalysts described herein are stable to a maximum overpotential of at least about 500, 550, 600, 650, 700, 750, 780, 800, 900, 1000, 1100, 1200 My or greater. For example, the catalysts described herein were subjected to a potential 300 mV higher than the limit reported for Nocera's catalyst (both at pH 7). No change in the catalyst/catalytic activity over 12 hours; little or no Co and/or P was found in the electrolyte solution when assayed using ICP-MS. The catalysts can be used in any of the commonly used buffer systems, such as borate, phosphate, nitrate, and/or sulfate.

The catalysts described herein can be prepared by a simple, scalable method that does not require electrochemical deposition or annealing.

Table 1 summarizes the performance differences between some of the catalysts described herein and catalysts known in the art.

TABLE 1

Summary of performance characteristics of various catalysts

| Catalyst | Co-based catalysts described herein (borate, pH 7) | Nocera (phosphate, pH 7) | Best Co oxide type Fe—Co—Ni Oxide (Berlingette) |
|---|---|---|---|
| Minimum Objective Overpotential (at 0.5 mA/cm$^2$) | 400 mV (linear at 275 mV) | 380 mV (linear at 275 mV) | 250 mV (linear at 190 mV) |
| Maximum Sustainable Overpotential | 780 mV | 480 mV | high |
| pH range | 6-16 | 4.5-9.5 | >13 |
| Electrolyte Limitations | Best in borate and hydroxide. Stable in all tested (acetate, phosphate, nitrate, sulfate, borate, hydroxide, zincate) | Only stable in strong proton acceptors (phosphate, borate) | Requires very high pH (KOH) and non-coordinating electrolyte |
| Other Drawbacks | | Must be prepared on conductive substrate | Difficult and expensive to prepare |

The catalysts described herein are stable at much higher overpotentials than Nocera's catalyst and are stable over a much broader pH range than the known best-forming Co-oxide catalysts. While the catalysts described herein and Nocera's catalysts are active at neutral pHs, Nocera's catalyst requires buffers having high proton accepting capacity. The catalysts described herein have little or no electrolyte limitations, which is in sharp contrast to Nocera's catalyst and Co-oxide catalysts.

III. Methods of Making the Catalysts

The catalysts can be prepared using various methods known in the art. The synthesis is a simple, scalable chemical reaction that does not require electrochemical deposition, ultra-high vacuum conditions, or annealing, which are drawbacks in many state of the art preparations. The synthesis is easily adaptable for use with other metals or ligands. It has been shown that small differences in ligand structure affect the activity profile of the catalyst. Therefore, one can have a high degree of control of catalyst properties based on selection of ligand.

A. Cobalt-Based Catalysts

In one embodiment, the cobalt-based catalysts are prepared by thermolysis of a solution of a suitable cobalt precursor, such as dicobalt octacarbonyl, and a suitable phosphine ligand, such as a bidentate phosphine (e.g., 1,2-bis(diphenylphosphino)ethane (dppe)) under an inert atmosphere.

The thermolysis reaction resulted in a decrease in mass by 20-28% (5-7 equiv. CO lost from $Co_2(CO)_8$). Subsequent aerobic oxidation of the resulting black precipitate at ambient temperature increased the mass by 5-12%, and afforded the resulting Co-dppe catalyst as a light brown, nanoparticulate precipitate.

TEM studies revealed roughly spherical particles with large size dispersity (15-300 nm in diameter) and a high degree of aggregation. EDX measurements from several particles of assorted sizes indicated an approximate Co:P ratio between 1:1 and 2:1.

Combined ICP-MS and C, H, N combustion analyses showed the resulting Co-dppe catalyst to have a bulk composition of 16.8% Co, 8.7% P, 45.3% C and 4.0% H by mass, indicating a stoichiometry of 2 Co atoms per molecule of dppe. No significant amount (<0.5 ppm) of Ir, Ru, Rh or Pt was found, excluding the possibility that the activity is due to impurities of these metals.

The FT-IR spectrum is distinct from those reported for CoO and $Co_3O_4$. Closer analysis indicates presence of metal-bound CO as well as cobalt oxide clusters. The small number of sharp Co-0 vibrational bands (500-800 cm$^{-1}$) suggests fairly small clusters of high symmetry, which are more likely modified oxocubane than adamantane structures.

Despite the insolubility of the resulting Co-dppe catalyst in every solvent tested, solid-state 31P NMR identified one broad signal ($\delta \approx 32$ ppm, 1.5 kHz width at half maximum). These values are consistent with those of known complexes of dppe and $^{59}$Co. Additionally, unmodified dppe was recovered by destructive distillation of the Co-dppe catalyst, indicating that the phosphine was not oxidized or otherwise covalently modified during the synthesis of the Co-dppe catalyst.

Glass slides with a 500 nm film of fluorine-doped tin oxide (FTO) on one side were used as electrodes. Application of a suspension of the Co-dppe catalyst in ethyl acetate to the FTO face of an electrode, followed by air-drying, afforded the active electrodes. Post-electrolysis SEM studies indicated that the catalyst particles become tightly bound to the surface with controllable filling fraction. "Tightly bound", as used herein, generally means that the catalyst remains adhered to the substrate under varying conditions, such as pH, solvent, etc. while retaining catalytic activity.

Cyclic voltammograms of an electrode with 1 mg of the Co-dppe catalyst in pH 6.8 phosphate buffer show a catalytic wave beginning near 1.25 V vs. NHE when compared to a naked FTO electrode control. The characteristics of the catalytic waves for catalysts formed with varied bidentate phosphines are, suggesting that the identity of the ligand does play a role in the activity of the nanoparticles formed after heating.

Tafel plots of catalytic currents in neutral conditions (5 different electrolytes, pH 7) show that this catalyst is active in proton-accepting media, suggesting a similar catalytic mechanism as Nocera's catalyst. However, electrochemically three important distinctions arise when comparing these materials: first, this Co-dppe catalyst does not noticeably degrade in buffers that are poor proton-acceptors reducing the need for a consistently buffered aqueous solution. Second, this catalyst is capable of sustaining current and water oxidation through high applied potentials, specifically in a borate buffer. No appreciable degradation of the catalyst was found in a pH 7 borate buffered solution after 12 hours with currents over 6 mA/cm$^2$. Third, Co-dppe is more active in borate electrolyte than in phosphate, whereas the opposite trend is true for Nocera's catalyst—it is less active in borate than in phosphate.

The intimate incorporation and lack of decomposition of the phosphine suggests that careful selection of ligand may allow for the tuning of the physical and chemical properties of material. Indeed materials produced by the same procedure, but with other bidentate phosphines, appear to be structurally similar to the Co-dppe catalyst, but display different activities as water oxidation catalysts. The shape of the catalytic waves for catalysts formed with varied bidentate phosphines are different, suggesting that the identity of the ligand does play a role in the morphology and catalytic activity of the nanoparticles formed after heating. The highest activity was observed in samples prepared using dppe. The robustness of this catalyst at high currents in proton accepting buffers and enhanced stability in buffers that are poor proton acceptors was attributed to the presence of a carbon backbone, present in SEM EDX, TEM EDX, and XPS of these materials.

The compositional and structural information obtained clearly indicate that the Co-dppe catalyst is not a simple cobalt oxide. These data do not strictly exclude the possibility that the activity is attributable to impurities of such compounds. However, comparison of the activity profiles of the Co-dppe catalyst with other known cobalt-based catalysts suggests that this is highly unlikely. $Co_3O_4$ is known to be significantly less active at neutral and acidic pH, than under basic conditions; however, the Co-dppe catalyst maintains activity in both neutral and strongly basic pHs. $Co_3O_4$ is also known to be unselective for the oxidation of water over the oxidation of chloride; however, the Co-dppe catalyst is highly selective for the oxidation of water in the presence of high concentrations of chloride. Nocera's catalyst was reported to be unstable in solutions not containing significant concentrations of phosphate or at high applied potentials; however, chronoamperograms of the Co-dppe catalyst show stability in sulfate at modest overpotentials and borate at much higher potentials. Finally, whereas Nocera's catalyst is more active in phosphate than in borate, the Co-dppe catalyst is more active in borate than in phosphate.

IV. Methods of Use

The catalysts described herein can be incorporated into the oxygen-producing anode of a variety of devices for purposes including, but not limited to, splitting water by electrolysis to produce hydrogen at the cathode, splitting water by electrolysis to produce oxygen at the anode, electrochemical oxidation of organic species at the anode, reducing metal ions to their corresponding metallic neutral state at the cathode, reduction of organic species by electrolysis at the cathode, reduction of any other species at the cathode, as long as it is coupled with oxygen production at the anode, and combinations thereof. These electrolytic processes can be driven by a variety of energy sources, such as solar, wind, and/or nuclear.

The catalysts described herein can also be incorporated into the oxygen-consuming cathode of a variety of devices including, but not limited to, oxygen-scavenging devices, oxygen-detectors, and fuel cells or batteries which consume oxygen (pure, or in mixtures, such as air, or specialty gas mixtures) in addition to any fuel including, but not limited to, hydrogen, organic fuels, metallic fuels, or inorganic fuels.

The catalysts described herein can also be used in conjunction with a chemical oxidant for the oxidation of organic species for synthetic or destructive purposes.

A. Water Oxidation

The water oxidation catalysts (WOCs) described herein can be used in a variety of devices. In one embodiment, the device is a cell containing an anode and a cathode. Water is oxidized at the anode in the presence of the WOC and hydrogen gas is evolved at the cathode. In some embodiments, the cathode contains a hydrogen evolution catalyst, for example, coated on the cathode surface. Suitable hydrogen evolution catalysts include, but are not limited to, tungsten disulfide, molybdenum disulfide, cobalt tetraimines, cyclopentadienyl ruthenium-nickel catalysts, samarium hydroxide, colloidal platinum catalysts stabilized by polyvinyl alcohol, dinuclear iron complexes, which are structural models of the active site of a type of enzyme (iron hydrogenases) which are efficient catalysts for hydrogen evolution, macrocyclic cobalt and nickel complexes, noble metals, and noble metal oxides and sulfides. Other hydrogen evolution catalysts are known in the art.

In other embodiments, water is oxidized at the anode, and metal ions are reduced to metals ($Zn^{2+} \rightarrow Zn$ or $Cu^+ \rightarrow Cu$ etc.) at the cathode. In some embodiments the metal is deposited as a coating on the cathode (electroplating, electrogalvanization), and in other embodiments the metal is deposited on the cathode as crystals, powder, foam or nodules, which may be removed from the cathode.

The anode and cathode can be made from materials known in the art. Such cells are known in the art and can be designed to conduct the reaction on any scale, including industrial scale. Alternatively, the reaction can be conducted in a cell in which the anode is irradiated with light resulting in the evolution of oxygen gas.

In still another embodiment, the reaction can be take place in the presence of a supramolecular system, such as a nanomaterial or nanostructure. Such systems can be used to imitate photosynthesis by conducting both water oxidation and proton reduction in the same molecular system. For example, in one embodiment, water is oxidized, in the presence of a WOC, at one end or part of a nanomaterial or nanostructure to produce oxygen, hydrogen ions, and electrons. The electrons are transported rapidly to another part of the nanomaterial or nanostructure, where a water reduction catalyst (hydrogen evolution catalyst) catalyzes the reduction of hydrogen ions by electrons to form hydrogen gas.

Supramolecular systems include molecular assemblies and composite materials. Exemplary materials include inorganic materials, such as high performance semiconducting nanomaterials and hierarchically assembled nanostructures. The materials can be designed to enhance light absorption, for example, by the incorporation of molecular antennae. Inorganic-organic hybrid materials with enhanced light absorption and tunable bandgaps can be used as platforms for the catalysts described herein. Other materials include nanotubes, nanosheets, etc., such as those prepared from $TiO_2$, other inorganic materials, and organic materials. Molecular assemblies can be prepared from polymers and polypeptides. Exemplary structures include polymer and coiled-coil polypeptide assemblies that can precisely position molecular subunits in three dimensions. Light harvesting assemblies prepared from polymers, such as one dimensional polymers, that absorb sunlight and efficiently transport the excited state energy over long distances can also be used. Finally, printing technology can be used to design, fabricate, and test nanostructured metal-oxide electrodes for improved light capture in solar fuel devices.

The hydrogen gas produced in the device described above can be separated from the oxygen gas. The hydrogen gas can be captured and stored until use. Alternatively, the devices described above can be linked to a hydrogen fuel cell or combustion reactor so that the hydrogen gas is fed directly into the end device. The product of hydrogen combustion/hydrogen consumption is water. This water can be recycled and reoxidized using the catalysts and methods of use described herein. Oxygen is also produced in the catalytic reaction. Oxygen can be capture and stored and used for a variety of applications which oxygen production is desirable.

The catalysts described herein can be incorporated into one or more of the devices discussed above or other devices suitable for water oxidation and the devices sold to the end user. Alternatively, the catalysts described herein can be provided in a kit. The kits contains the catalyst in a container, along with instructions for use of the catalyst, and the end user incorporates the catalyst into one of the devices discussed above or another device useful for water oxidation. For industrial scale processes, the amount of catalyst to be used can vary from milligrams to grams to kilograms to tons. One of ordinary skill can readily determine the amount of catalyst need for a particular application on a particular scale.

For water oxidation, the minimum overpotential required for sustaining current greater than 1 $mA/cm^2$ for the catalysts described herein is about 400 mV at pH 7. While this value is higher than that exhibited by Nocera's catalyst (e.g., 380 mV), Nocera's catalyst degrades at overpotentials of 480 mV or greater while the catalysts described herein are stable and continue to be active at overpotentials greater than 780 mV. The buffers that can be used with the catalysts described herein are significantly less expensive than the buffers required for Nocera's catalyst.

B. Electrochemical Fuel Cells

A fuel cell is generally an electrochemical cell that converts a source fuel into an electrical current and water. It generates electricity inside a cell through reactions between a fuel and an oxidant, triggered in the presence of an electrolyte. The reactants flow into the cell, and the reaction products flow out of it, while the electrolyte remains within it. Fuel cells can operate virtually continuously as long as the necessary flows are maintained.

Fuel cells are different from conventional electrochemical cell batteries in that they consume reactant from an external source, which must be replenished, a system known as a thermodynamically open system A hydrogen fuel cell uses hydrogen as its fuel and oxygen (usually from air) as its oxidant. Other oxidants, such as chlorine or chlorine dioxide can also be used. Examples of hydrogen fuel cells include, but are not limited to, proton exchange fuel cells, solid oxide fuel cells, and molten carbonate fuel cells.

Applications of hydrogen fuel cells include power sources for automobiles and other vehicles, such as industrial equipment and power sources for remote locations, such as remote weather stations, large parks, rural locations, and in certain military applications. Hydrogen fuel cells can also be used to power small electronic devices where AC charging may not be available for weeks at a time, such as notebook computers, portable charging docks for small electronics (e.g. a belt clip that charges your cell phone or PDA), smartphones, GPS units, and small heating appliances. A fuel cell system running on hydrogen can be compact and lightweight, and have no major moving parts. Because fuel cells have no moving parts and do not involve combustion, they have high reliability, resulting in minimum down time.

D. Oxidation of Organic Compounds

The catalysts detailed herein can be used for the synthesis of commodity and specialty chemicals that are made by oxidation of precursor organic species possessing C—H bonds. This can be as a single step of a multi-step synthesis to form a complex product, as a stand-alone catalytic reaction to transform one chemical into another single chemical or group of chemical products, or to oxidatively degrade harmful or unwanted organic compounds to less harmful compounds such as acetate, formate, carbonate, and/or carbon dioxide. Oxidants that can be used with this catalyst include, but are not limited to, electrochemical oxidants (an applied electric potential), chemical oxidants including, but not limited to, Oxone, potassium hydrogen peroxysulfate ($KHSO_5$), hydrogen peroxide, oxygen, ozone, or a combination of chemical and electrochemical oxidants.

Applications of carbon-hydrogen bond oxidation using this catalyst include bulk commodity chemical synthesis, remediation of organic waste, and synthesis of specialty chemicals due to selective oxidation of specific carbon-hydrogen bonds in an organic species.

EXAMPLES

Materials

Commercially available xylenes (J. T. Baker, A.C.S. Reagent grade), 1,2-bis(diphenylphosphino)ethane (Aldrich, 97%), Xantphos (Strem), 2,2'-bis(diphenylphosphino) diphenyl ether (Aldrich), nitric acid (BDH, 67-70%, trace metals analysis grade), sulfuric acid (J. T. Baker, 96%, ACS Reagent Grade), potassium phosphate monobasic (Sigma Life Science, >99.0%), hydrogen peroxide (J. T. Baker, 30%, A.C.S. Reagent grade), potassium nitrate (Acros Organics, A.C.S. Reagent grade), sodium sulfate (Aldrich, A.C.S. Reagent grade), sodium acetate (Aldrich, A.C.S. Reagent grade), sodium tetraborate decahydrate (borax, Mallinckrodt, A.C.S. Reagent grade), boric acid, and potassium hydroxide (J. T. Baker, ACS Reagent Grade) were used as received.

Dicoablt octocarbonyl (Strem, stabilized with 1-5% hexane) could be used as received, but required recrystallization from pentane after long periods (acceptable if bright orange or red, but no darker).

Potassium bromide (Acros Organics, 99+%, spectroscopic grade), was dried over an open flame in a Schlenck flask under vacuum immediately prior to use.

Example 1. Catalyst Synthesis

In a nitrogen-filled glovebox, a 25×150 mm threaded Pyrex test tube was charged with dicobalt octocarbonyl (345 mg, 1.01 mmol), 1,2-bis(diphenylphosphino)ethane (399 mg, 1.00 mmol) and a large Teflon-coated magnetic stirbar, and sealed with a Teflon screw-cap with a small silicone septum. The tube was suspended over a rapidly rotating magnetic stir plate, and xylenes (5.0 mL, freshly sparged with dry nitrogen for 30 minutes) were added in one portion by syringe (immediate and rapid evolution of carbon monoxide was observed).

The mixture was stirred at ambient temperature until effervescence ceased (24° C., ca. 5 minutes). The tube was evacuated briefly and refilled with dry nitrogen. The tube was inserted 2 cm deep into a 160° C. stirring polyethylene glycol bath. The reaction mixture rapidly reached a stable reflux and was stirred vigorously for 90 minutes at reflux. Stirring continued as the mixture was allowed to cool to ambient temperature, whereupon the cap was removed and the mixture was stirred open to the atmosphere for 65 hours.

The reaction mixture was split evenly and transferred to two centrifuge vials with ethyl acetate (8.0 mL final volume in each tube). The tubes were centrifuged at 5000 rpm for 10 minutes, the dark supernatant was removed from the pale tan precipitate, and fresh ethyl acetate was added (8.0 mL). This process was repeated until the supernatant was colorless, and then once more without adding more solvent (6 centrifugations total). Drying under vacuum afforded the product catalyst (428 mg) as a free-flowing light tan to grey powder.

Mass Balance Studies

Trials were conducted in triplicate (precise data in table below). Small Teflon-coated stirbars were placed in glass vials (9×85 mm, Exetainer® by Labco Limited), and their combined mass recorded (open to air). The vials were brought into a nitrogen-filled glovebox and were charged with ca. 100 μmol each of $Co_2(CO)_8$ (freshly recrystallized from pentane) and dppe. The vials were then each sealed with a threaded cap with a Teflon/rubber layered septum, and removed from the glovebox. Xylenes (800 freshly sparged with dry nitrogen for 30 minutes) was added by syringe, and the resulting mixture was stirred at ambient temperature for 5 minutes, before being inserted into a 2 cm deep aluminum heating block, and stirred for 1.5 hours at 160° C. The vials were then removed and allowed to cool to ambient temperature. Volatiles were removed by vacuum, and the contents were dried for 15 hours at ambient temperature and <1 Torr. The caps were removed, and the precise mass of each vial, including stirbar and solid products, was determined (open to air). Xylenes (800 μL) was added to each vial by syringe, and the resulting mixtures were stirred open to the atmosphere for 65 hours at ambient temperature. Volatiles were removed by vacuum, and the contents were dried for 15 hours at ambient temperature and <1 Torr. The caps were removed, and the precise mass of each vial, including stirbar and solid products, was determined (open to air). A summary of the data is shown in Table 2.

EDX spectra were taken using silicon monoxide coated TEM grids (Ted Pella, Product #01829) in order to monitor carbon content in the as-synthesized material. For studies of sample alteration after prolonged electrolysis in different electrolytes, scanning electron microscope (SEM) images and SEM-EDX spectra of the as-deposited and post-electrolysis electrodes were taken using the electrode preparation procedure described below and a Hitachi SU-70 SEM.

X-Ray Diffraction

Powder samples of 1, dppe and dppeO2 were subjected to 1.5418 Å radiation using a Bruker aXS D8 Focus spectrometer with a Cu source (40 mA, 40 kV), with a stationary sample holder. The spectra below were recorded using a 0.02° increment and 5 or 10 second exposure time per data point.

The diffraction pattern of dppeO2 and that observed in samples of Co-dppe are very similar, but not identical. The peaks are shown in Table 3.

TABLE 3

| | Peak locations | |
|---|---|---|
| Co-dppe | dppeO$_2$ | dppeO$_2$ (continued) |
| 7.78 | 6.98 | 19.18 |
| 11.04 | 7.74 | 19.78 |
| 11.52* | 9.94 | 20.94 |
| 15.54 | 11.04 | 21.90 |
| 17.10 | 15.40 | 22.18 |
| 23.40* | 16.09* | 23.30* |
| 24.30 | 16.28* | 24.30 |
| | 17.06 | 25.00 |

The signal-to-noise apparent in the spectra of Co-dppe suggests that only a very small proportion of the sample is crystalline. These data could indicate minor contamination with crystallites of Co-dppe, which are a different crystalline phase than that observed for the pure compound.

ICP-MS

Before analysis, the catalyst was digested according to a modification of a published procedure. A sample of the

TABLE 2

Summary of mass balance data

| Trial | A | B | C |
|---|---|---|---|
| Mass of vial + stirbar | 11.446 g | 11.7645 g | 11.8234 g |
| Mass of Co$_2$(CO)$_8$ | 34.0 mg | 36.7 mg | 34.5 mg |
| | 99.4 μmol | 107.3 μmol | 100.9 μmol |
| Mass of dppe | 39.6 mg | 42.5 mg | 40.5 mg |
| | 99.4 μmol | 106.7 μmol | 101.7 μmol |
| Δ Mass for thermolysis | −15.1 mg | −17.7 mg | −21.4 mg |
| | −20.5%$^a$ | −22.3%$^a$ | −28.5%$^a$ |
| | 539 μmol CO$^b$ | 632 μmol CO$^b$ | 764 μmol CO$^b$ |
| | 5.4 equiv. CO$^c$ | 5.9 equiv. CO$^c$ | 7.6 equiv. CO$^c$ |
| Δ Mass for aeration | +2.7 mg | +3.3 mg | +6.6 mg |
| | +3.7% | +4.2% | +8.8% |
| Δ Mass total | −12.4 mg | −14.4 mg | −14.8 mg |
| | −18.8% | −18.2% | −19.7% |

$^a$% = 100 × (Δ Mass)/([mass Co$_2$(CO)$_8$] + [mass dppe]).
$^b$Assuming all mass lost is released CO.
$^c$Making previous assumption, and calculating based on moles of Co$_2$(CO)$_8$.

Characterization of Catalyst

Microscopy/EDX

High resolution transmission electron microscopy (TEM) and energy dispersive x-ray spectroscopy in the TEM (TEM-EDX) were used to determine particle size, crystallinity (or lack thereof), and elemental composition with an FEI Tecnai Osiris TEM operating at 200 kV. TEM images and TEM-catalyst (11.5 mg) was combined with 1.00 mL nitric acid (70%, trace metals analysis grade) in a vial, which was sealed with a plastic screw-cap containing a Teflon-lined septum. The mixture was heated in a 100° C. oil bath for 30 minutes and allowed to cool to ambient temperature. Aqueous hydrogen peroxide (1.00 mL, 30%) was added to the mixture, and the mixture was heated in a 100° C. oil bath for 30 minutes (the vial was vented with a 20 G needle for 3 seconds, to relieve excess pressure, after 3 minutes of heating). The mixture became turbid upon cooling to ambient temperature, so another portion of aqueous hydrogen peroxide (1.00 mL, 30% was added), and the mixture was heated in a 100° C. oil bath for an additional 30 minutes. The resulting solution remained homogeneous upon cooling to ambient temperature, and even when immersed in a 0° C. ice bath for 20 minutes.

The resulting solution was diluted to 25.00 mL with nanopure water in a volumetric flask. A 500 µL aliquot was diluted to 50.0 mL with 2.0% nitric acid (trace metals analysis grade), and subjected to analysis. This solution was found to contain 405 µg/L $^{31}$P and 771 µg/L $^{59}$Co, which indicates 1 is comprised of 8.710% P, w/w, 16.797% Co (1:0.987 P/Co molar ratio). A summary of the data is shown in Table 4.

TABLE 4

Summary of elemental analysis

| Sample | P-31 (ppb) | Co-59 (ppb) | Ru-101 (ppb) | Rh-103 (ppb) | Ir-191 (ppb) | Pt-194 (ppb) |
|---|---|---|---|---|---|---|
| 1 | 405 | 771 | 0.00026 | 0.00070 | 0.00094 | 0.00000 |
| 2 | 405 | 787 | 0.00000 | 0.00062 | 0.00026 | 0.00000 |
| 3 | 392 | 760 | 0.00008 | 0.00043 | 0.00058 | 0.00000 |
| Average | 401 | 773 | 0.00028 | 0.00058 | 0.00059 | 0.00000 |

Elemental Analysis

Combustion elemental analyses were conducted in duplicate by Robertson Microlit, using an additional oxidant. The results are displayed in the

TABLE 5

Elemental analysis of C, H, and N

| Sample | C | H | N |
|---|---|---|---|
| 1 | 45.39% | 3.94% | <0.02% |
| 2 | 45.18% | 4.00% | <0.02% |

Temperature Programmed Desorption:

A U-shaped quartz tube (5×30 mm) was charged with 1 (2.8 mg). A constant flow of dry helium (50 mL/min) was used to purge the tube for 10 minutes, and maintained throughout the experiment. A small, but consistent percentage of the exhaust flow was diverted to a mass spectrometer (Stanford Research Systems RGA100, employing an electron-impact ionizer, a quadrupole mass filter and a Faraday cup ion detector) over the course of the experiment, and the masses of $H_2O$ (m/z=18), CO (m/z=28), and $CO_2$ (m/z=44) were monitored. After adequate purging, the quartz tube was inserted into a programmable heating chamber, heated at a rate of 10° C./min. to 100° C., held constant at 100° C. for 10 minutes, and then heated at a rate of 10° C./min to 890° C.

By the time the sample reached 300° C. it had lost $H_2O$, CO, and $CO_2$ in a 3.19:1.91:1 molar ratio (3.73 µmol/mg (6.7% w/w), 2.23 µmol/mg (6.2%) and 1.17 µmol/mg (5.2%), respectively) (calibrated with calcium oxalate, monohydrate, which releases the gases in a strict 1:1:1 molar ratio).

Destructive Distillation

As shown in FIG. 1, 16×150 mm test tube 10 was charged with 27.1 mg of catalyst 12 and sealed with a rubber septum 14. The septum 14 was pierced with a 22 G needle, and connected to a vacuum line 16 (pressure<1 Torr throughout distillation). The base 75 mm of the tube was heated to 250° C. 20 in a kugelrohr furnace 18. The other half of the tube was cooled in a stream of liquid nitrogen 22, which was expelled from a plastic wash bottle 24. After 2 hours subjected to these conditions, the tube was brought into a nitrogen-filled glovebox. The lower portion of the tube, containing the residue was cut off. The portion of the tube containing the sublimate was washed into a flask using dichloromethane.

After concentration under vacuum, the sublimate was dissolved in $CDCl_3$ and identified as dppe by NMR. The amount was determined to be 220.0 µmol by integration against an internal standard. This accounts for 32.4% of the mass of added 1 (% of the ligand expected to be contained in 27.1 mg of 1).

Solubility Studies

Aliquots of the catalyst (3-8 mg) were combined with 1.0 mL quantities of the following solvents: acetonitrile, chloroform, dimethyl carbonate, dimethylformamide, dimethylsulfoxide, 1,2-dimethoxyethane, ethyl acetate, ethylene glycol, methanol, nitromethane, pyridine, triethylamine and water. Even after prolonged stirring and sonication, no detectable $^{31}$P signal was found in any of the supernatants.

Solid State NMR

The MAS NMR was run on 500 MHz wide-bore Varian INOVA spectrometer with a 9.5 mm Chemagnetics MAS probe spinning at 3.5 kHz. The magic angle was adjusted with KBr, and the 31P chemical shift was referenced to liquid phosphoric acid, taken as 0 PPM. The pulse width was 30 degrees, the relaxation delay was 60 seconds, and the number of scans was 1260. Total acquisition time was 21 hours.

As the MAS speed was low compared with the very broad 31P chemical shift tensor, we observed a lot of rotational sidebands. Because of limited 1H decoupling power, the center line of the $^{31}$P spectrum was also very broad, around 1.5 kHz. In order to determine the isotropic chemical shift, we ran another experiment with 3 kHz MAS. Comparing these two data sets, we assigned 32 ppm as the isotropic chemical shift position. As the center peak was very broad, we were not able determine how many isotropic peaks are present.

IR

Spectroscopy grade KBr (112 mg, anhydrous) and 1 (2.4 mg) were mixed together and cast into a pellet using a die and a hydraulic press (2000 psi applied). The pellet was then analyzed with a Midac M1200 spectrometer, purged with a constant flow of dry nitrogen gas (2 ml/min.).

Electrochemistry

Deposition

A suspension of 1 in ethyl acetate (100 µL EtOAc per mg of 1) was prepared by sonication (60 seconds, Branson 2510). 100 µL/in.$^2$ of the suspension was then spread evenly over the surface of a FTO-coated glass slide (TEC 7, 1×1 in, 2.2 m thickness, Hartford Glass Co. Inc.). The electrode was allowed to dry in air for at least 20 minutes before being cut in half. From these electrodes 1 cm×1 cm active areas were cut out and measured to ensure an accurate calculation of geometric surface area. The electrode was immersed in an electrochemical cell and electrochemical measurements were taken with a Princeton Applied Research Versastat 4-400 potentiostat/galvanostat using a standard three electrode set-up, with the sample as the working electrode, a platinum wire as the counter electrode, and an Ag/AgCl reference (Bioanalytical Systems, Inc., NHE vs. Ag/AgCl:

+197 mV). All experiments were performed without IR compensation using 0.1 M buffer at pH 7, unless stated otherwise.

CVs

Figure 2:
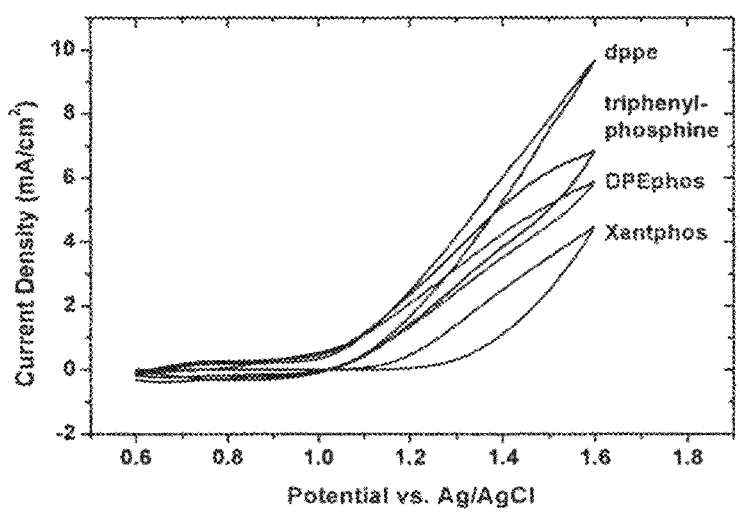
FIG. 2 is a graph showing cyclic voltammograms of cobalt catalysts with different organophosphines incorporated: dppe; Xantphos; triphenylphosphine; and DPEphos.

Cyclic voltammograms were used to determine performance of catalytic materials made using different organophosphine ligands. To ensure that the samples were stable throughout the CV, samples were equilibrated at 1.2 V vs. Ag/AgCl for 4 minutes beforehand and no major increase or decrease in current was observed. Below are CVs for cobalt-phosphine materials made with four different organophosphines, with blue, red, black and green denoting dppe, Xantphos, triphenylphosphine, and DPEphos, respectively. Scan rate: 10 mV/s, 0.1 M potassium phosphate, pH 6.8, no IR compensation, Pt wire counter electrode, Ag/AgCl reference, solution was gently stirred to assist mass transport of $O_2$ bubbles. The results are shown in FIG. 2.

Tafel Plots

Figure 3:
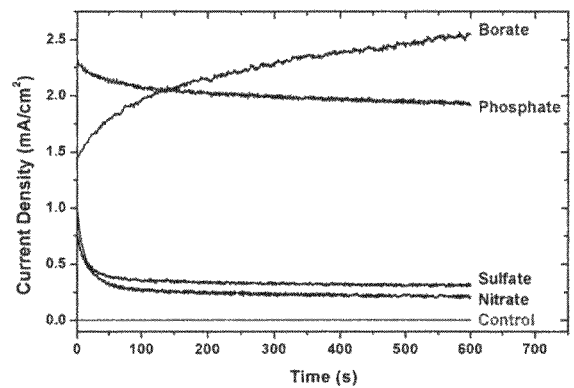
FIG. 3 is a graph showing 10 minute chronoamperograms of samples at 1.2 V vs. Ag/AgCl taken prior to Tafel plots at pH 7 in 0.1 M nitrate, sulfate, acetate, phosphate, and borate buffers. Control samples were taken in different buffers using an FTO/glass slide without any catalyst (grey).

Co-DPPE samples were tested for current stability prior to collection of Tafel plot data. Samples in nitrate, sulfate, and acetate did not experience an increase or decrease in current over 10 minutes at 1.2 V vs. Ag/AgCl. Phosphate buffer caused a slight decrease in current, which we attribute to replacement of phosphine by $PO_4^{2-}$. Samples in borate buffers showed a steady increase in current which lasted approximately 1 hour, and were allowed to stabilize before obtaining Tafel plot data. This was attributed to incorporation of borate into the catalyst. Unlike previously discovered Co—Bi catalysts, however, we still see spectroscopic evidence of phosphorus (from dppe) in EDX spectra after >2 hours of water oxidation at 1.4 V vs. Ag/AgCl suggesting that it plays a role in this catalyst's enhanced stability compared to other Co—Bi materials. Tafel plots were taken while the solution was stirred at 25 mV steps between 0.75 V vs. Ag/AgCl and 1.4 V vs. Ag/AgCl with a 10 second rest time between data points. After initial spikes in current caused from capacitance, steady-state values were attained within approximately 2 minutes and plotted in FIG. 3.

Figure 4:
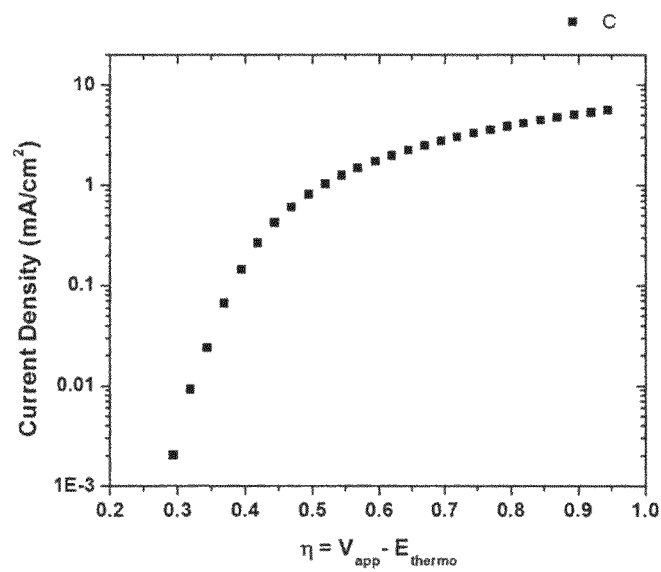
FIG. 4 is a graph showing the Tafel plot of Co-dppe in pH 13 NaOH.

Electrochemistry in basic conditions was performed using an FTO electrode with a catalyst surface loading of 0.42 mg/cm$^2$, and 0.10 M NaOH. After equilibration (10 minutes, 0.80 V vs Ag/AgCl), the Tafel plot was taken at 25 mV steps between 0.360 and 1.210 V vs Ag/AgCl with a 5 second rest time between data points. Amperometric data was recorded for 5 minutes at each potential, and values for the last 2.5 minutes were averaged to afford the value included in the Tafel plot. The results are shown in FIG. 4. The slope of the linear region is 63 mV/decade.

Oxygen detection was performed with a TauTheta MFPF-100 KHz using phase fluorometry (calibrated with argon [Tech Air] and air). A 250 mL three-neck round bottom flask was charged with 0.1 M borate electrolyte (leaving ca. 60 mL headspace). A large, Teflon-coated stirbar was used to agitate the electrolyte gently. The flask was thermostated at 25° C. A reference electrode (Ag/AgCl), the working electrode, and a Pt wire counter electrode were each inserted through large rubber septa, and the oxygen detector was inserted through the rubber septum with the anode. The septa were then inserted into the necks of the flask such that the electrodes were all submerged and tip of the fluorescence probe was ca. 3 cm above the surface of the electrolyte.

Once assembled, the septa were secured with Parafilm® and electrical tape. The flask was purged with argon (which was bubbled through the electrolyte, not just the headspace) until the oxygen level reached a stable minimum. The purge was ceased, and the oxygen level monitored for 30 minutes to be sure that there was no leakage. A constant potential of 1.4 V vs the Ag/AgCl reference electrode was then applied for 60 minutes, and oxygen detection was maintained until oxygen levels reached a stable maximum. The headspace volume was determined to be 55.0 mL at the end of the experiment.

Stability Studies and Post-Electrolysis Analyses

Figure 5:
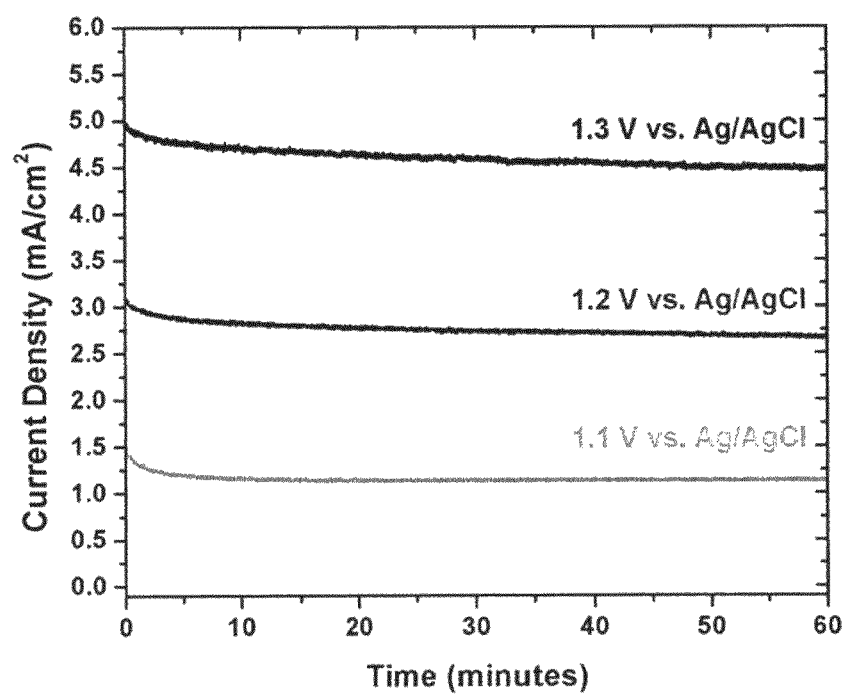
FIG. 5 is a graph showing hour-long chronoamperograms of Co-dppe in phosphate buffer at pH 7 at 1.1 V vs. Ag/AgCl (bottom), 1.2 V vs. Ag/AgCl (middle), and 1.3 V vs. Ag/AgCl (top).

Chronoamperograms at varied potentials for one hour in sulfate, borate, and phosphate buffers were performed using the conditions outlined above. No decay in current or of the catalyst deposited on the FTO electrode was seen for any applied potential in a borate buffer. In sulfate, no decrease in current or degradation of catalyst was seen at 1.1 V vs. Ag/AgCl (1.3 V vs. NHE) or 1.2 V vs. Ag/AgCl (1.4 V vs. NHE), while a slight decrease in current can be seen at 1.3 V vs. Ag/AgCl (1.5 V vs. NHE) and finally a significant decrease in current and degradation of catalyst at 1.4 V vs. Ag/AgCl (1.6 V vs. NHE). In phosphate, chronoamperograms show stable current at 1.1 V vs. Ag/AgCl (1.3 V vs. NHE), however at all higher potentials there is a slow degradation of current observed as shown in FIG. 5.

After 2 hours of electrolysis at 1.4 V vs, Ag/AgCl (1.6 V vs. NHE), the Co-dppe retains phosphorus as shown by SEM-EDX. Similar retention of phosphorus is seen in sulfate buffered samples after 2 hours of electrolysis.

Figure 6A:
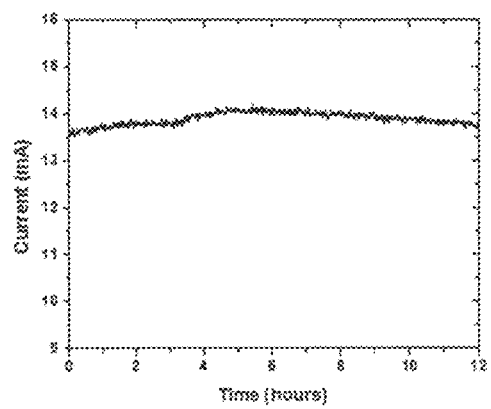
FIGS. 6A and 6B are graphs showing current stability data for a Co-dppe sample with geometric surface area 1.45 cm$^2$ showing both continuous 12 h stability at 1.6 V vs. NHE (left) and stable activity over a one hour time course after >40 h intermittent use (right). Brief drops and spikes observed in the current in the inset figure are caused by oxygen bubble formation and release.
Figure 6B:
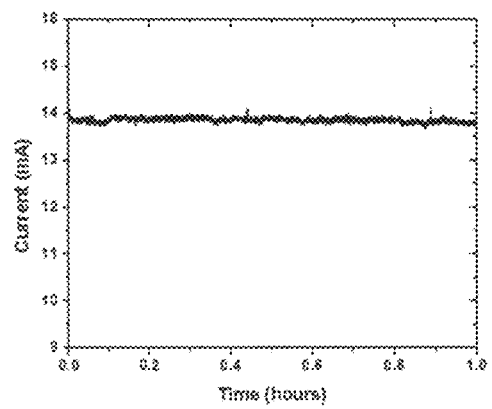

Long-term stability studies were performed in a two-compartment electrochemical cell with each compartment separated by a glass frit. 12 hour uninterrupted stability at 1.4 V vs. Ag/AgCl was investigated. The results show that after over 40 hours of intermittent use at varied potentials between 1.1 V vs. Ag/AgCl and 1.4 V vs. Ag/AgCl high activity is still retained. See FIGS. 6A-6B.

Figure 7:
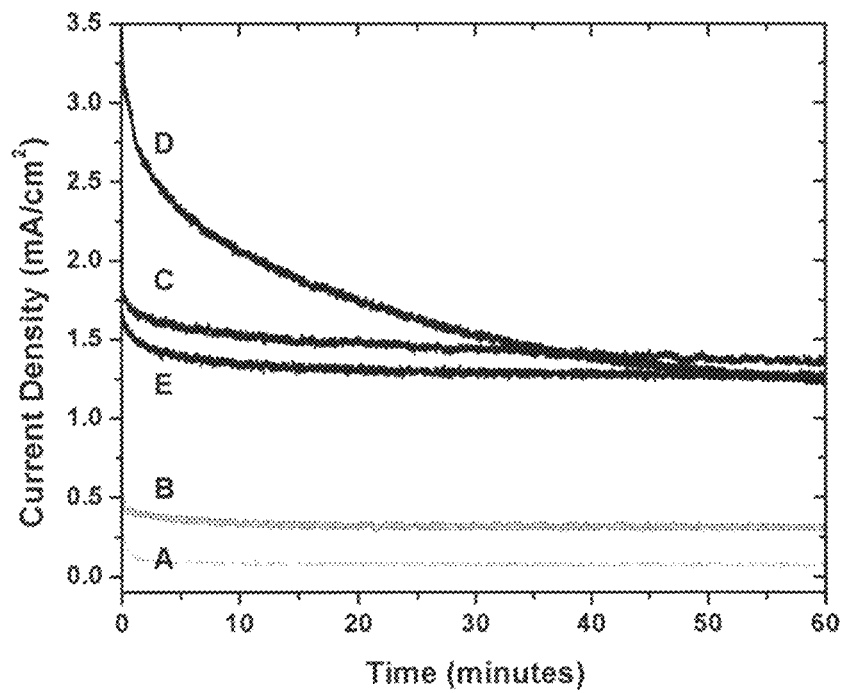
FIG. 7 is a graph showing a 1 hour chronoamperogram in a pH 7 sulfate buffered solution at potentials of 1.1, 1.2, 1.3, and 1.4 V vs. Ag/AgCl and a 1 hour chronoamperogram in the same sulfate solution (at 1.3 V vs. Ag/AgCl) using a sample previously used for 12 h of water oxidation in borate at 1.4 V vs. Ag/AgCl. Activity in a weakly basic electrolyte is still present.

While electrolysis in borate appears to cause a change in the catalyst, it is reversible. Upon immersing a sample in a sulfate buffered solution after 12 h of electrolysis in a borate buffered solution, its prior activity is retained. See FIG. 7.

XPS Analysis

FTO electrodes (one blank [A], one with fresh catalyst deposited on it [B], one with catalyst that had undergone >40 h electrolysis in borate [C], and one with catalyst that had undergone electrolysis in sulfate [D]) were sent to CAMCOR (at the University of Oregon) for XPS analysis. Spectra were taken on a ThermoScientific ESCALAB 250 instrument, employing monochromatized X-rays from an aluminum source. Pass energies of 150 eV and 20 eV were used for survey and composition scans, respectively. In both cases a beam-width of 500 μm was used.

Loading Studies

Suspensions of 1 in ethyl acetate were prepared in the following manner: A 20 mL scintillation vial (A) was charged with 1 (2.4 mg) and ethyl acetate (12.0 mL). Another vial (B) was charged with ethyl acetate (12.0 mL). Vial A was sonicated briefly and well mixed just before a portion (1.00 mL) of the suspension was transferred to vial B. Portions of each suspension (500 μL) were thoroughly applied to FTO-electrodes (A and B), while a third electrode was treated with 500 μL of ethyl acetate only. After drying for 30 minutes, the electrodes were assessed by chronoamperometry at 1.6 V vs NHE in pH 7.0 0.1 M borate electrolyte. Current densities reported in Table 6 are averages of the current density over the last five minutes of a 20-minute CA.

TABLE 6

Average current densities

| Electrode | A | B | Blank |
|---|---|---|---|
| µM 1/cm² | 15.5 | 1.29 | 0 |
| mA/cm² | 0.540 | 0.538 | 0.018 |
| Calculated moles of (O₂)/Co atom · h | 93 | 1120 | NA |

Differentiation from Co-Pi and Co₃O₄

Electrolysis was conducted in either 0.1 M borax at pH 7 or in 0.1 M phosphate at pH 7. The working electrode was either: an FTO electrode activated with Co-Pi by the method published, 2 an FTO electrode with Co3O4 deposited on it, an FTO electrode with 1 deposited on it, or an FTO electrode with 1 deposited on it which had been run at 1.4 V vs Ag/AgCl in 0.1 M borate for 12 h before beginning the experiment. Platinum mesh was used for the counterelectrode, and Ag/AgCl as the reference. Each of the plates was subjected to 6 consecutive 1 h chronoamperometry experiments at 1.40 V vs Ag/AgCl in alternating fresh 20 mL electrolyte solutions (borate, then phosphate, then borate, then phosphate etc.). All electrodes were rinsed with 18 MΩ deionized water before introduction to the new electrolyte. The setup was such that the three electrodes were always in the same position relative to each other, to ensure minimal change in current due to resistivity. The currents in the Table 7 are average values for the last 10 minutes of each hour-long run, which clearly demonstrate three different behaviors: Co-Pi, which is better in phosphate than in borate; Co₃O₄ which is worse in each successive run; and 1 which is better in borate than in phosphate.

TABLE 7

Average current values

| | Co—Pi | Co₃O₄ | 1 | 1 after 12 hrs |
|---|---|---|---|---|
| Borate | 1.6 mA | 0.9 mA | 1.7 mA | 0.8 mA |
| Phosphate | 3.4 mA | 0.7 mA | 0.4 mA | 0.5 mA |
| Borate | 1.6 mA | 0.6 mA | 0.8 mA | 0.7 mA |
| Phosphate | 3.2 mA | 0.3 mA | 0.3 mA | 0.3 mA |
| Borate | 1.5 mA | 0.3 mA | 0.7 mA | 1.0 mA |
| Phosphate | 3.0 mA | 0.3 mA | 0.3 mA | 0.2 mA |

Example 2. Scaled Up Catalyst Synthesis

A 250 mL round-bottom flask equipped with a large Teflon-coated stirbar and a reflux condenser sealed with a rubber septum was filled with dry nitrogen. The reflux condenser was removed, and dicobalt octacarbonyl (22.8 g) was added quickly, before replacing the condenser. The flask was purged with dry nitrogen for 15 minutes. Xylenes (50 mL, sparged with nitrogen) was added by syringe and the reaction vessel was placed above a magnetic stirplate. Once the dicobalt octacarbonyl was fully dissolved, a stream of dry nitrogen was passed through the headspace of the reaction flask and was vented through a bubbler. A suspension of 1,2-bis(diphenylphosphino)ethane (26.4 g) in xylenes (110 mL, sparged with nitrogen) was added quickly by cannula. Evolution of CO gas was observed. The reaction mixture was heated to 160° C. (reaching reflux) and stirred vigorously for one hour. The reaction vessel was allowed to cool for 30 minutes before the condenser was removed. The reaction mixture was stirred vigorously, open to the air, for 4 days. The resulting heavy suspension was filtered using a Buchner funnel, and washed with ethyl acetate until the filtrate was colorless. The remaining brown powder was dried under vacuum, yielding the catalyst (22.0 g).

Stability in Strongly Basic Electrolytes

The catalysts described herein are stable in strongly basic electrolytes (e.g., pH 12 to 30 wt % KOH) for extended periods of time, for example, greater than two months.

Figure 8:
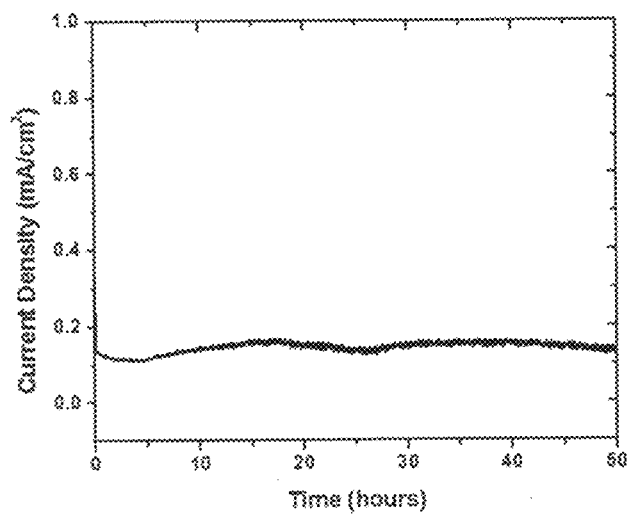
FIG. 8 is a graph showing continuous current stability for 50 h with a Co-dppe sample with geometric area 1.45 cm$^2$ in water collected from the Long Island Sound that has been passed through a 0.2 micron filter, but otherwise unadulterated.
Figure 9:
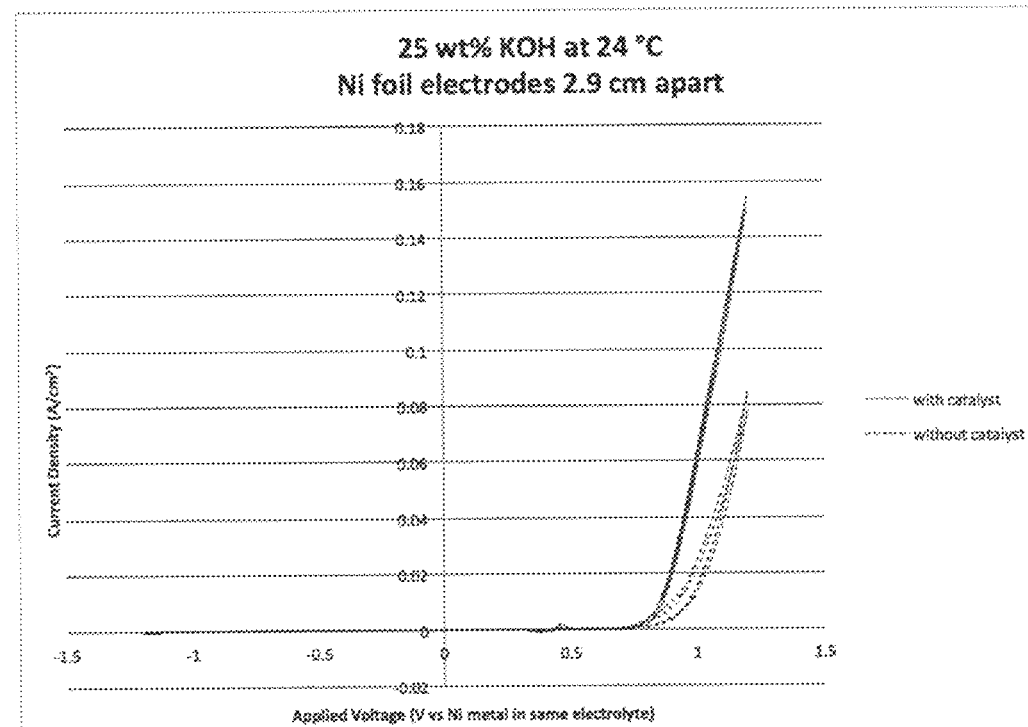
FIG. 9 is a graph showing current density (A/cm$^2$) as a function of applied voltage (V vs Ni metal in same electrolyte) for catalyst-coated and uncoated nickel electrodes in 25 wt % potassium hydroxide.

The results are shown in FIG. 8. A suspension of Co-dppe was prepared in etheyl acetate (9.9 mg/mL), and sonicated for 20 seconds. 100 µL of the suspension was applied to each side of a nickel electrode (28 mm×12.5×0.127 mm), and allowed to air dry (about 5 minutes, each). This electrode was used as the anode, in conjunction with cathode consisting of only nickel foil (28 mm×12.5×0.127 mm). Two nickel foil electrodes (28 mm×12.5×0.127 mm) were connected to a potentiostat as the counter electrode (cathode) and reference electrode. The anode with catalyst deposited on it was attached as the working electrode (anode), separated from the counter electrode and reference electrode by approximately 2.9 cm each. Approximately 1.6 cm of each electrode was submerged in a 25 wt % solution of KOH in deionized water. Cyclic voltammetry from −1.20 to 1.20 V vs the reference electrode was performed at 50 mV/second, at room temperature. An electrochemical setup identical to the first, but employing an anode lacking catalyst (nickel foil only) was subjected to the same conditions as a control. The results are shown in FIG. 9.

The system employing catalyst was shown to be more active than the control: the system with catalyst achieved a current density of 0.01 A/cm² at a potential 69 mV lower than the control, and 0.05 A/cm² 147 mV lower. The catalytic system achieved a current density between 75% and 450% greater than the control system across the voltage range of 800 mV to 1200 mV. This experiment also demonstrated that the catalyst is stable under both oxidizing and reducing applied potentials (−1.2 to +1.2 V vs Ni foil in same electrolyte).

Example 3. Synthesis and Characterization of Related Catalysts

Inside a N₂ atmosphere glovebox, a stock solution of Co₂(CO)₈ was prepared by weighing 975 mg into a Schlenk bomb and adding 39 mL of N2 sparged xylenes. The ligands 1,2-ethanediylbis[diphenylphosphine oxide], DPEphos, triphenylphosphine, 1,2-Bis(1-piperidinyl)ethane, TMEDA, EDTA, 4,4'-bipyridine, 2,2'-bipyridine, dppm, dppe, dppb, and dppp were weighed out into reaction tubes in an equimolar ratio to the Co₂(CO)₈ (except PPh₃ 2 mol eq). The tubes were sealed, evacuated and refilled with N₂ three times.

Under nitrogen, 3 mL of the cobalt solution was added to each tube. The reactions were allowed to stir for 30 min under nitrogen purge. The tubes were heated to 160° C. for 90 min. The reactions were cooled to room temperature and allowed to stir open to air for 36 hrs. The reactions were centrifuged down and decanted. The solids were washed with ethyl acetate, centrifuged, and decanted until the solution was still clear after separation. The resulting solids were dried on high vacuum. IR spectra were recorded for each material.

Approximately 1 mg of each material was suspended in 250 µL of ethyl acetate by sonicating and then drop casting onto fresh FTO electrodes. The electrodes were allowed to dry overnight before electrochemical measurements were made. The electrochemical measurements were carried out in a small beaker with 40 mL 0.1 M borate electrolyte pH 7. An Ag/AgCl reference electrode was used along with platinum mesh as the counter electrode. Each sample underwent a 1.2 V (vs Ag/AgCl) applied potential for 4 min prior to recording a CV for the material. A CV was recorded from 0.2 to 1.4 V at a scan rate of 10 mV/sec. The results are shown in FIGS. 10A-M.

Figure 10A:
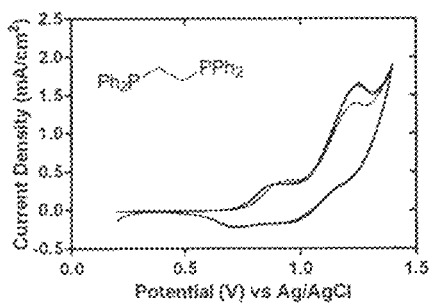
FIGS. 10A-M are cyclic voltammograms (3 cycles each) in pH 7.0 borate of cobalt-based catalysts with different ligands. The ligands are shown structurally in each voltammogram Materials formed from $CO_2(CO)_8$ and dppe, (FIG. 10A), 1,2-ethanediylbis[diphenylphosphine oxide] (FIG. 10B), DPEphos (FIG. 10C), triphenylphosphine (FIG. 10D), 2,2'-bipyridine (FIG. 10E), TMEDA or EDTA (FIG. 10F); materials formed from 1,2-Bis(1-piperidinyl)ethane (FIG. 10G), dppm (FIG. 10H), dppb (FIG. 10I), dppp (FIG. 10J) and $N^1,N^{1'},N^2,N^{2'}$-tetramethylethane-1,2-diamine (FIG. 10K); 4,4'-bipyridine (FIG. 10L)
Figure 10B:
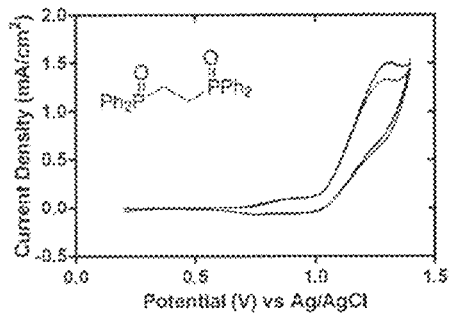
Figure 10C:
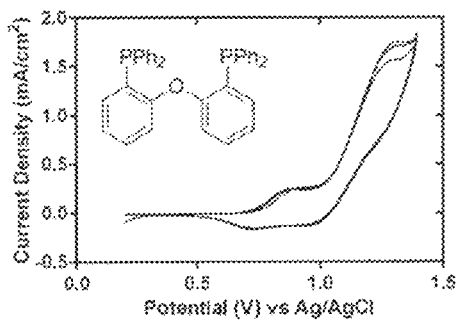
Figure 10D:
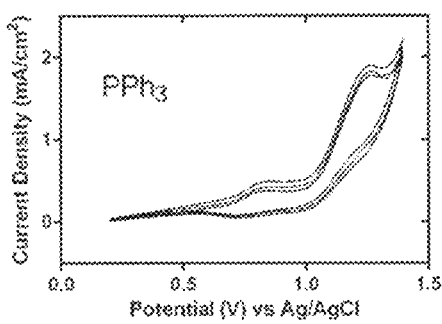
Figure 10E:
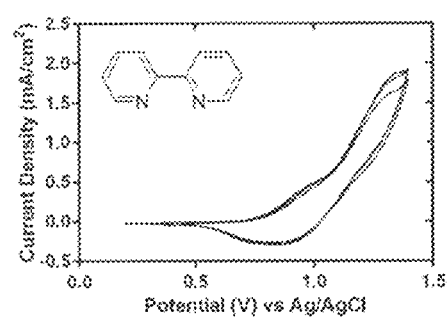
Figure 10F:
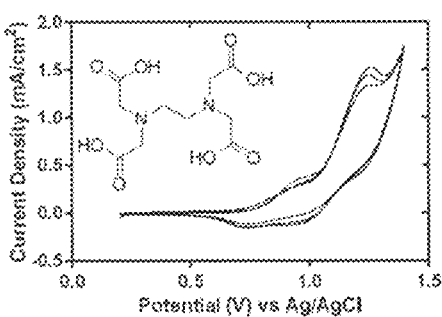
Figure 10G:
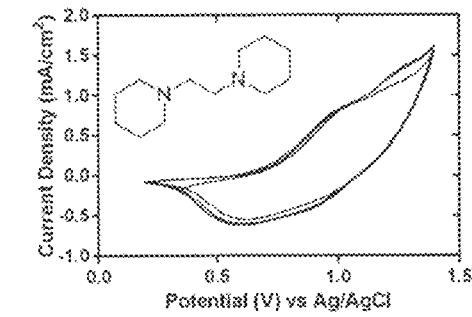
Figure 10H:
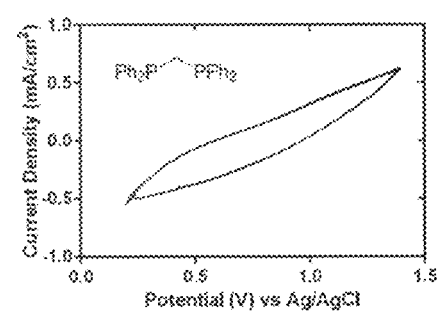
Figure 10I:
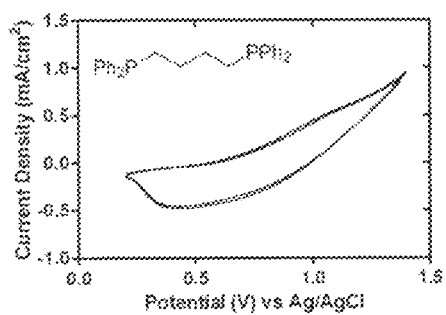
Figure 10J:
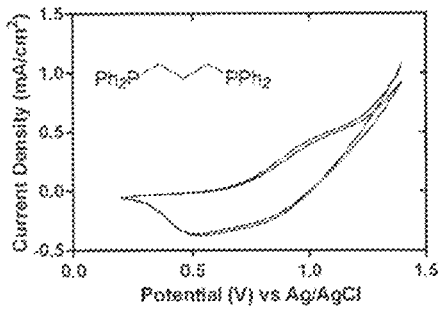
Figure 10K:
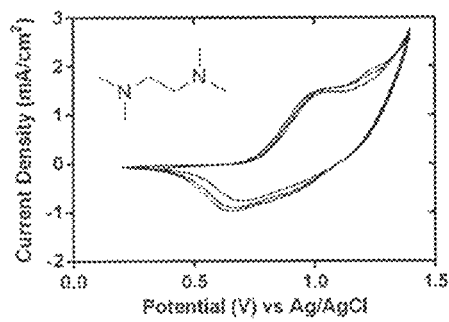
Figure 10L:
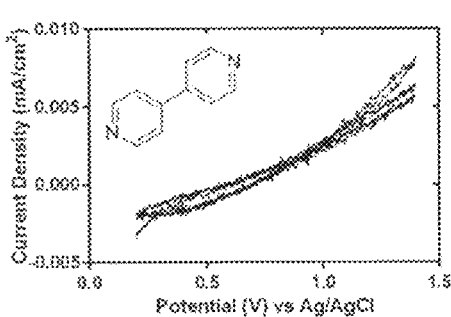
Figure 10M:
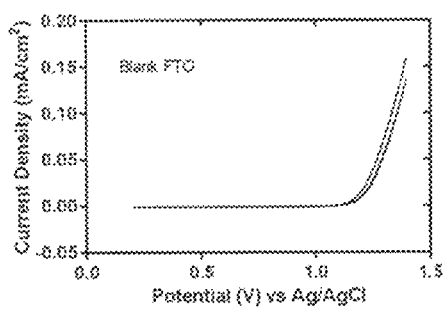

Materials formed from $CO_2(CO)_8$ and dppe, (FIG. 10A), 1,2-ethanediylbis[diphenylphosphine oxide] (FIG. 10B), DPEphos (FIG. 10C), triphenylphosphine (FIG. 10D), 2,2'-bipyridine (FIG. 10E), TMEDA or EDTA (FIG. 10F), were found to be very active as water oxidation catalysts. Materials formed from 1,2-Bis(1-piperidinyl)ethane (FIG. 10G), dppm (FIG. 10H), dppb (FIG. 10I), dppp (FIG. 10J) and $N^1,N^{1'},N^2,N^{2'}$-tetramethylethane-1,2-diamine (FIG. 10K) were found to be somewhat active as water oxidation catalysts. The material formed from 4,4'-bipyridine (FIG. 10L) was found to be inactive as a water oxidation catalyst, and formed non-conductive film on the electrode, ultimately deactivating it for water oxidation. FIG. 10M is a negative control without catalyst.

Example 4. Electrolytic Production of Zinc from Alkaline Solutions of Zinc Oxide Preparation of the "Activated Electrode"

A suspension of Co-dppe was prepared in etheyl acetate (9.9 mg/mL), and sonicated for 20 seconds. 100 μL of the suspension was applied to each side of a nickel electrode (28 mm×12.5×0.127 mm), and allowed to air dry (about 5 minutes, each).

Preparation of the "30 g/L Zinc Electrolyte"

Zinc oxide (15.0 g) was dissolved in 500 mL of a pre-formed 25 wt % solution of sodium hydroxide in deionized water, resulting in a homogeneous solution.

Preparation of the "Saturated Zinc Electrolyte"

Zinc oxide (20.0 g) was added to 150 mL of pre-formed "30 g/L Zinc Electrolyte" and stirred vigorously overnight. The slurry was then allowed to settle for 1 hour, and the milky suspension (the "Saturated Zinc Electrolyte") was decanted from the majority of undissolved zinc oxide.

Electrolysis 1 (Control with No Catalyst in "30 g/L Zinc Electrolyte")

A PET beaker was filled with "30 g/L Zinc Electrolyte" (120 mL). Three nickel foil electrodes (28 mm×12.5×0.127 mm) were connected to a potentiostat as the working electrode (anode), counter electrode (cathode) and reference electrode. Approximately 1.6 cm of each electrode was submerged. Cyclic voltammetry from 0.5 to 1.40 V vs the reference electrode was performed at 5 mV/second at room temperature. (Hydrogen bubbles begin forming on the nickel cathode at 1.20 V on the first cycle, and from the zinc-coated cathode around 1.24 V thereafter). A constant voltage of 1.20 V vs the reference electrode was then applied, at room temperature, for 6 hours, inducing a current that started at 3.4 mA/cm$^2$ and increased to 22.1 mA/cm$^2$ by the end (calculated based on submerged anode surface area which remained constant throughout electrolysis.)

Electrolysis 2 (with Catalyst in "30 g/L Zinc Electrolyte")

A PET beaker was filled with "30 g/L Zinc Electrolyte" (120 mL). Two nickel foil electrodes (28 mm×12.5×0.127 mm) were connected to a potentiostat as the counter electrode (cathode) and reference electrode. An "Activated Electrode" was attached as the working electrode (anode). Approximately 1.6 cm of each electrode was submerged. Cyclic voltammetry from 0.5 to 1.40 V vs the reference electrode was performed at 5 mV/second, at room temperature. A constant voltage of 1.20 V vs the reference electrode was applied, at room temperature, for 16 hours, inducing a current that started at 15.5 mA/cm$^2$ and increased to 44.4 mA/cm$^2$ by hour 6, and up to 63.3 mA/cm$^2$ by the end (calculated based on submerged anode surface area which remained constant throughout electrolysis.) The "Activated Electrode" was removed and rinsed with deionized water. The electrode was shown to remain activated for water oxidation.

Electrolysis 3 (Control with No Catalyst in "Saturated Zinc Electrolyte")

A PET beaker was filled with "Saturated Zinc Electrolyte" (120 mL). Three nickel foil electrodes (28 mm×12.5×0.127 mm) were connected to a potentiostat as the working electrode (anode), counter electrode (cathode) and reference electrode. Approximately 1.6 cm of each electrode was submerged. Cyclic voltammetry from 0.5 to 1.40 V vs the reference electrode was performed at 5 mV/second at room temperature. A constant voltage of 1.20 V vs the reference electrode was applied, at room temperature, for 60 seconds, inducing a current that started at 5.0 mA/cm$^2$ and decreased to 3.3 mA/cm$^2$ by the end (calculated based on submerged anode surface area which remained constant throughout electrolysis.) A second constant voltage of 1.30 V vs the reference electrode was applied, at room temperature, for 120 seconds, inducing a current that started at 7.3 mA/cm$^2$ and decreased to 6.5 mA/cm$^2$ by the end (calculated based on submerged anode surface area which remained constant throughout electrolysis.)

Electrolysis 4 (with Catalyst in "Saturated Zinc Electrolyte")

The setup described in "Electrolysis 3" was modified by replacing the working electrode (anode) with the "Activated Electrode" used in "Electrolysis 2." Cyclic voltammetry from 0.5 to 1.40 V vs the reference electrode was performed at 5 mV/second at room temperature. A constant voltage of 1.20 V vs the reference electrode was applied, at room temperature, for 300 seconds, inducing a current that started at 21.2 mA/cm$^2$ and remained constant (calculated based on submerged anode surface area which remained constant throughout electrolysis.)

A second constant voltage of 1.30 V vs the reference electrode was applied, at room temperature, for two hours, inducing a current that started at 37.5 mA/cm$^2$ and increased to 46.6 mA/cm$^2$ by the end (calculated based on submerged anode surface area which remained constant throughout electrolysis.)

A third constant voltage of 1.40 V vs the reference electrode was applied, at room temperature, for 45 minutes, inducing a current that started at 63.1 mA/cm$^2$ and increased to 70.8 mA/cm$^2$ by the end (calculated based on submerged anode surface area which remained constant throughout electrolysis.)

A fourth constant voltage of 1.50 V vs the reference electrode was applied, at room temperature, for 300 seconds, inducing a current that started at 87.9 mA/cm$^2$ and decreased to 85.3 mA/cm$^2$ by the end (calculated based on submerged anode surface area which remained constant throughout electrolysis.)

A fifth constant voltage of 2.20 V vs the reference electrode was applied, at room temperature, for 50 minutes, inducing a current that started at 195.59 mA/cm2 and increased to 255.5 mA/cm2 by the end (calculated based on submerged anode surface area which remained constant throughout electrolysis.)

After these experiments, the "Activated Electrode" was removed and rinsed with deionized water. The electrode was shown to remain activated for water oxidation, and analysis by SEM and SEM/EDX showed the catalyst was still bound to the surface, morphologically unchanged and not contaminated with any zinc.

Figure 11A:
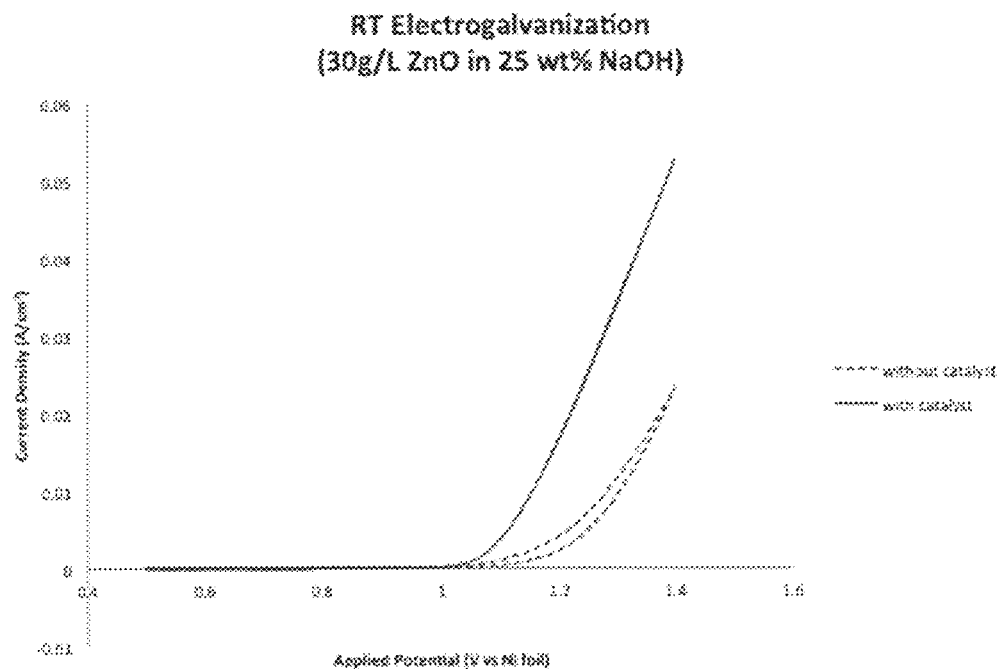
FIG. 11A is a graph showing current density (A/cm$^2$) as a function of applied potential (V vs Ni) with catalyst and no catalyst in 25 wt % sodium hydroxide and 30 g/L zinc oxide.
Figure 11B:
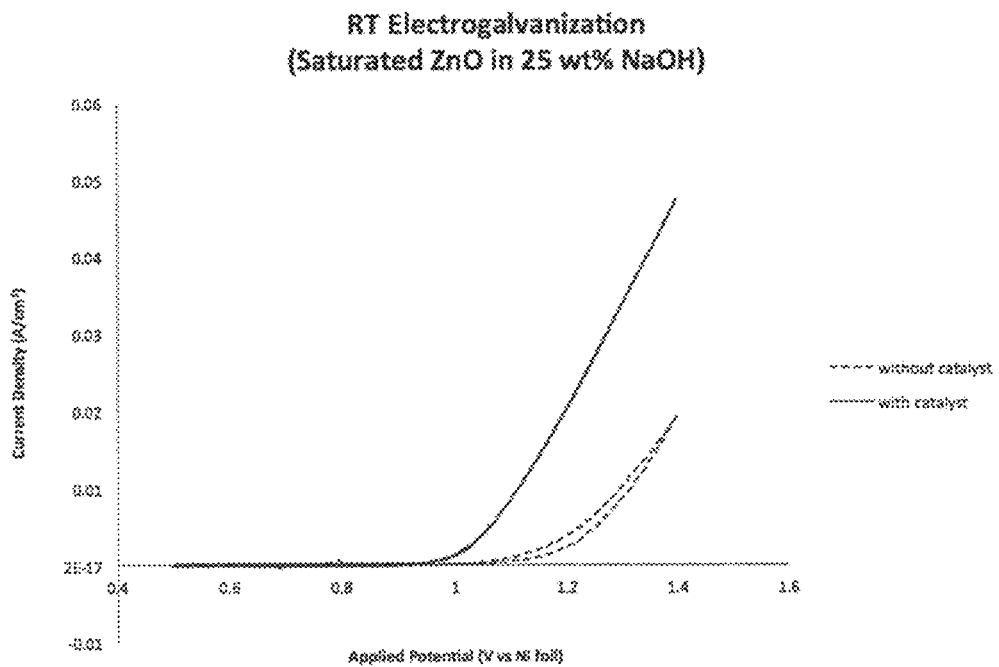
FIG. 11B is a graph showing current density (A/cm$^2$) as a function of applied potential (V vs Ni) with catalyst and no catalyst in 25 wt % sodium hydroxide saturated with zinc oxide.
Figure 12A:
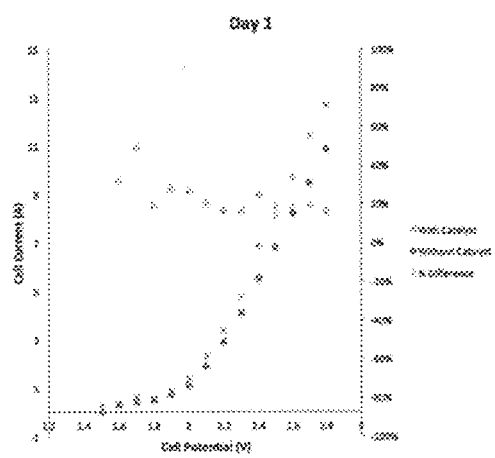
FIGS. 12 A-F are graphs showing cell current (A) as a function of cell potential (V) with and without catalyst at day 1, 13, 20, 34, 42, and 50.
Figure 12B:
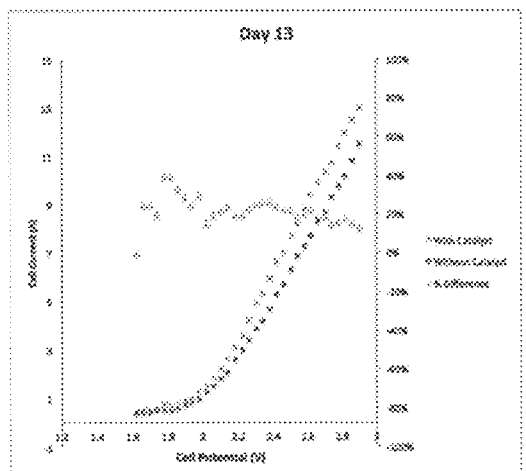
Figure 12C:
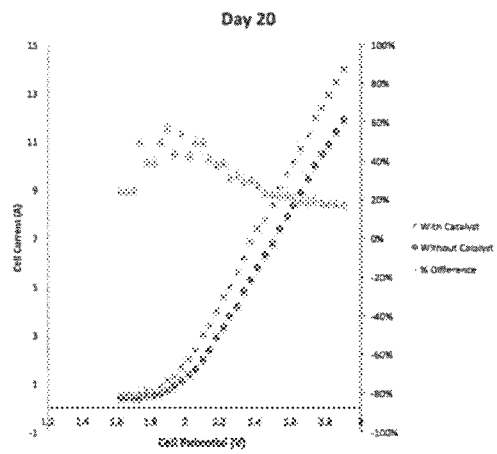
Figure 12D:
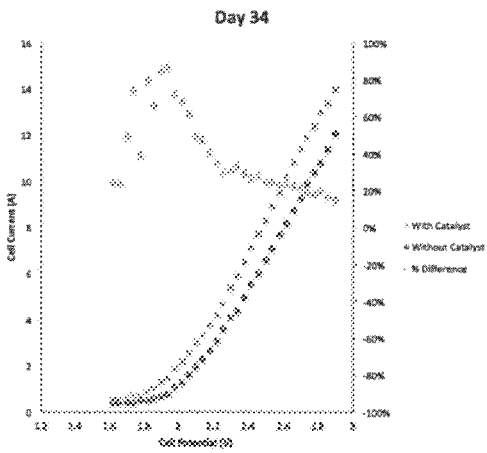
Figure 12E:
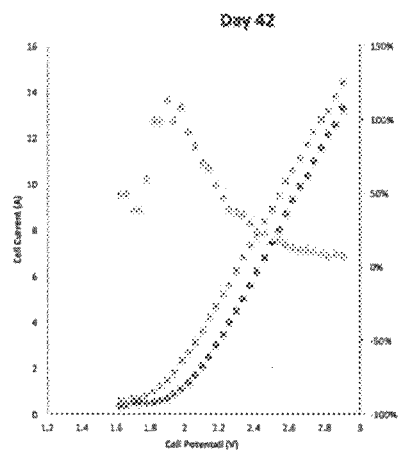
Figure 12F:
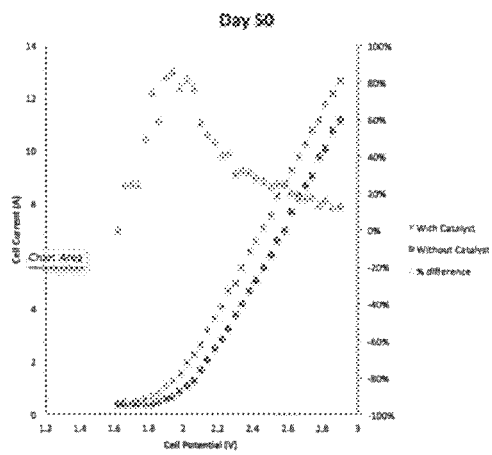

The current density as a function of applied potential (V vs Ni) for catalyst and no catalyst is shown in FIGS. 11A and B. The experiment comparing nickel electrodes with and without catalyst in the electrolyte saturated with zinc oxide demonstrated that the catalyst significantly increased the activity, allowing a current density of 0.005 A/cm$^2$ at a potential 160 mV lower than the identical setup without catalyst, and a current of 0.01 A/cm$^2$ at a potential 195 mV lower. The cells without catalyst have nearly identical performance in both high and lower zinc concentrations, while the cells with catalyst have significantly lower onset potential at higher zinc concentration. This indicates that the cathodic zinc reduction reaction is rate limiting in cases where the anode is activated with catalyst, while the anodic water oxidation reaction is rate limiting in cases without any catalyst. These experiments also demonstrate stability of the catalyst in the presence of high concentrations of zinc over extended periods of time.

Example 5. Hydrogen Electrolyzer Study

A dry-cell alkaline electrolyzer consisting of six stainless steel plates (two terminal plates and four bipolar plates), separated by 3-mm neoprene gaskets, was disassembled. A suspension of 224 mg Co-dppe in 25.0 mL ethyl acetate was sonicated for 45 seconds. 4.0 mL portions of the suspension were applied to one face of each of the four bipolar plates, and both faces of one of the terminals. After air-drying, these plates were reassembled such that the faces of the bipolar plates with catalyst were directed at the terminal plate without catalyst (see FIG. 16).

The electrolyzer was connected to a reservoir filled with 1N NaOH electrolyte, and run at a constant current of 5.0 A for 50 days. The electrolyte level was maintained by adding deionized water ever 2 or three days, as needed, and the electrolyzer was drained, rinsed and refilled with new 1N NaOH every 7 to 12 days. After each refill, the electrolyzer was subjected to a study in which the applied voltage was adjusted between 8.1 and 14.5 V (1.62-2.9 V/cell). The current was measured at each potential, and recorded. Another dry-cell alkaline electrolyzer of the same dimensions, but without catalyst was filled with the same electrolyte each time, and used as a control for each study. The two electrolyzers are compared in FIGS. 12A-F over periods of time of one day (12A), 13 days (12B), 20 days (12C), 34 days (12D), 42 days (12E), and 50 days (12F).

This study shows that activation of the electrolytic cell improves output by at least 20% (up to 100%) at a given voltage in the range of nominal working conditions, and that this improvement is long-lived: surviving >50 days of continuous operation and at least 5 complete electrolyte replacements and rinses of the cell.

Example 6. Electrochemical Oxidation of Glycerol

A solution of 0.9 M glycerol and 1.1 M NaOH in D$_2$O was prepared as electrolyte. An H-cell with a coarse glass frit separating the anodic and cathodic chambers was filled with the electrolyte (45 mL). An FTO electrode with 680 mg 1 per cm$^2$ was used as the anode, a platinum mesh was used as the cathode, and a silver wire submerged in the anolyte was used as the reference electrode. The voltage was adjusted to achieve the greatest current without observing bubble formation (oxygen production) at the anode. A potential of 0.9 V (vs Ag wire reference) was found to be optimal. After 72 hours, an aliquot of the anolyte was analyzed by $^1$HNMR (acetic acid added as internal standard for integration). Formate was found to be the major product (89% Faradaic yield), with traces of lactic acid (~1% Faradaic yield).

Example 7. Oxidation of Organic Compounds Using Chemical Oxidants

Oxidant Screens for C—H oxidation

Sodium ethylbenzene sulfonate was used as a test substrate for C—H oxidation. A variety of common oxidants were screened for activity with the catalyst. Stock solutions of sodium ethylbenzene sulfonate and each oxidant were prepared by adding degassed D$_2$O and the respective oxidant by syringe into tubes under N$_2$ atmosphere (if oxidant was solid it was added prior to flushing tubes with N$_2$). Reaction tubes with stirbars and 1 mg of catalyst (e.g., Co-dppe) were evacuated under vacuum and flushed with N$_2$ several times before adding stock solution of the sodium ethylbenzene sulfonate. The reactions were initiated by addition of the stock solution of oxidant. After 1 hour, a stock solution of d$_4$-sodium trimethylsilyl propionate (NMR internal standard) and d$_6$-dimethylsulfoxide (oxidant quench) in D$_2$O was added. The reactions stirred another 15 min and then were filtered into NMR tubes. The reaction yield was quantified by NMR using the internal standard. Reaction conditions: 20 µmol sodium ethylbenzene sulfonate, 100 µmol oxidant, 1 mg catalyst (e.g., Co-dppe), 500 µL D$_2$O; under N$_2$ at room temperature for 1 hr.

Oxone and its isolated active component, KHSO$_5$, were determined to be the only oxidants that showed any appreciable activity for the oxidation of sodium ethylbenzene sulfonate under these conditions.

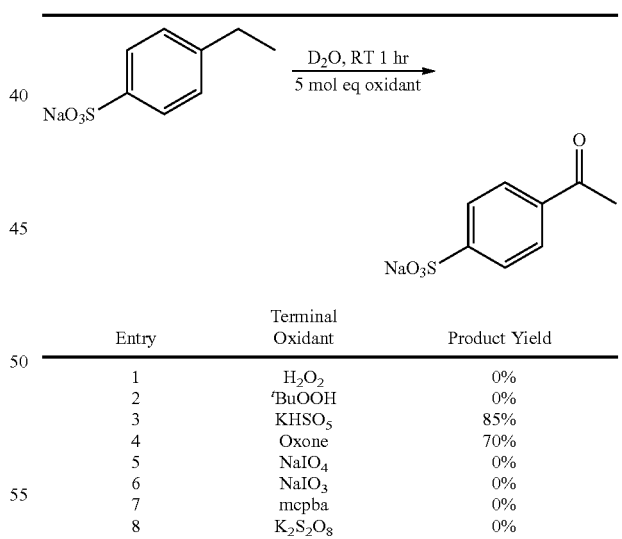

| Entry | Terminal Oxidant | Product Yield |
| --- | --- | --- |
| 1 | H$_2$O$_2$ | 0% |
| 2 | $^t$BuOOH | 0% |
| 3 | KHSO$_5$ | 85% |
| 4 | Oxone | 70% |
| 5 | NaIO$_4$ | 0% |
| 6 | NaIO$_3$ | 0% |
| 7 | mcpba | 0% |
| 8 | K$_2$S$_2$O$_8$ | 0% |

Conditions:
20 umol EBS, 100 umol oxidant, 1 mg 1, 500 uL D$_2$O RT, 1 hr under N$_2$;
NMR yields determined by d$_4$-TMSP standard Substrate Screen (Selective Oxidation)

Several substrates were screened for C—H oxidation using the catalyst (e.g., Co-dppe) and KHSO$_5$. The general conditions for the screen were: 20 µmol sodium ethylbenzene sulfonate, 100 µmol oxidant, 1 mg catalyst (e.g., Co-dppe), 500 µL 4:1 d$_6$-acetone:D$_2$O; under N$_2$ at room temperature.

A stock solution of KHSO$_5$ was prepared in degassed D$_2$O under N$_2$. Catalyst (e.g., Co-dppe) was added to each reaction tube. The tubes were then evacuated under vacuum and refilled with N$_2$ several times. 400 μL of d$_6$-acetone was added to each tube followed by the appropriate substrate. Reactions were initiated by the addition of 100 μL of KHSO$_5$ stock solution. Reactions were monitored for 3 or 15 hrs depending on the substrate. The reactions were quenched by addition of a stock solution of d$_4$-sodium trimethylsilyl propionate (NMR internal standard) and d$_6$-dimethylsulfoxide (oxidant quench). The reactions stirred another 15 min and then were filtered into NMR tubes. The reactions were quantified by NMR. (Control reactions were performed without catalyst and in each case the substrate conversion is >5%)

For most of the substrates selective oxidation to a single product was observed. The catalyst system was able to oxidize unactivated alkanes to a single product but in low yield. Oxidation of 1-butanol illustrates the difference the catalyst and simple cobalt salts. The catalyst selectively oxidizes butanol to butyric acid whereas the Co(II) salts tested were highly unselective, affording several different products.

| Rxn | Substrate | Major Product | % yield | Mass balance |
|---|---|---|---|---|
| 1[b] | Cyclohexane | Cyclohexanone | 20 | 60 |
| 2[b] | Styrene | 1-Phenyl-1,2-ethanediol | 36 | 72 |
| 3[a] | THF | γ-butyrolactone | 42 | >95 |
| 4[a] | Butanol | Butyric acid | 70 | >95 |
| 5[b] | Cumene | Acetophenone | 31 | 79 |
| 6[b] | 2-hexanone | Acetonylacetone | 15 | 93 |
| 7[b] | Pyrrolidine | 2-Pyrrolidinone | 95 | >95 |
| 8[b] | Benzyl alcohol | Benzoic acid | 51 | 93 |
| 9[b] | Cyclopentanol | Cyclopentanone | 47 | 66 |
| 10[b] | Ethylbenzene sulfonate | 4-acetophenone sulfonate | 90 | >95 |
| 11[b] | D-sec-phenethyl alcohol | Acetophenone | 75 | >95 |
| 12[b] | Ethyl benzene | Acetophenone | 46 | 85 |

[a]Reaction time 3 hrs
[b]Reaction time 15 hrs

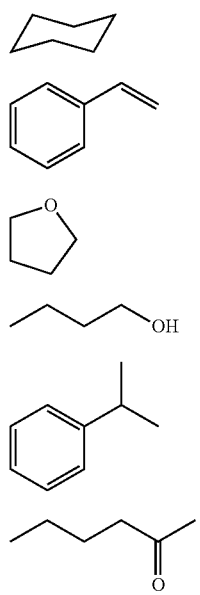

1

2

3

4

5

6

7

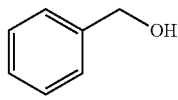

8

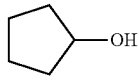

9

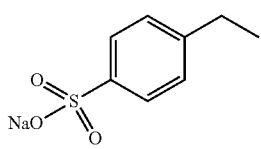

10

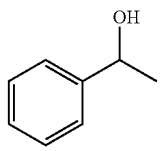

11

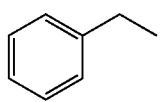

12

Water Oxidation Vs Chemical C—H Oxidation

The vessel shown below was charged with 6 mg of catalyst (e.g., Co-dppe) and then evacuated under vacuum and refilled with nitrogen several times. A stock solution of sodium ethylbenzene sulfonate in degassed D$_2$O was added to the vessel. The oxygen concentration was monitored with a TauTheta MFPF-100 KHz using phase fluorometry (calibrated with argon [Tech Air] and air). The reaction was initiated by addition of stock KHSO$_5$ in degassed D$_2$O. The reaction was monitored for 1 hr after which a stock solution of d$_4$-trimethylsilylpropionate and d$_6$-DMSO in D$_2$O were added. The reaction was stirred an additional 15 min then filtered into an NMR tube for analysis. The C—H oxidation was quantified by proton NMR. The conditions were as follows: 120 μmol sodium ethylbenzene sulfonate, 600 μmol KHSO5, 6 mg catalyst (e.g., Co-dppe), and 3 mL D$_2$O.

After 1 hr 120 μmol of sodium acetophenone sulfonate and 2.7 μmol of O$_2$ were measured. The system is highly selective for C—H oxidation over water oxidation. Many catalysts that are capable of water oxidation are incapable of selective C—H oxidation over water oxidation. In this system, combination of the catalyst (e.g., Co-dppe) and oxidant seems to be below the oxidation potential for water oxidation while still high enough to oxidize many types of C—H bonds.

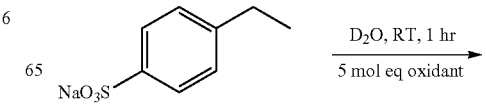

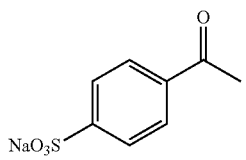

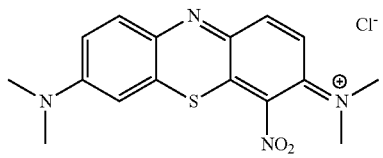

Methylene Green

Pollutant Remediation

The catalyst was used to attempt to mineralize common persistent environmental pollutants. Catalyst (e.g., Co-dppe) and substrates were weighed into reaction tubes and 400 µL of $d_6$-acetone was added. The reactions were initiated by addition of $KHSO_5$ in $D_2O$. Reactions were carried out open to air at room temperature. A stock solution of $d_4$-trimethylsilylpropionate and $d_6$-DMSO in $D_2O$ were added. The reaction was stirred an additional 15 min then filtered into an NMR tube for analysis. NMR yields calculated by internal standard Conditions: 20 µmol substrate, 100 µmol oxidant, 1 mg catalyst (e.g., Co-dppe), 500 µL 4:1 $d_6$-acetone:$D_2O$. The pollutants were dibenzodioxin, dibenzofuran, and 1,4-dioxane, the structure of which are shown below:

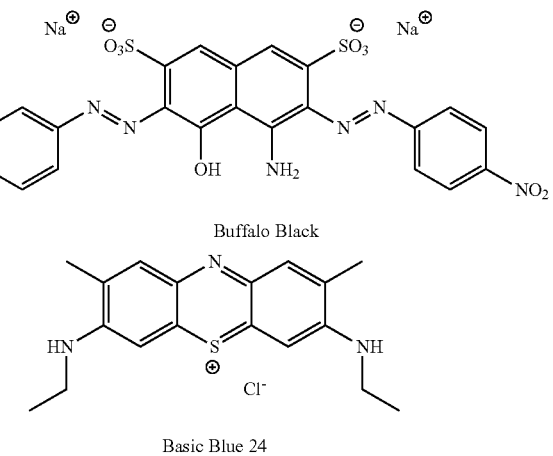

Buffalo Black

Basic Blue 24

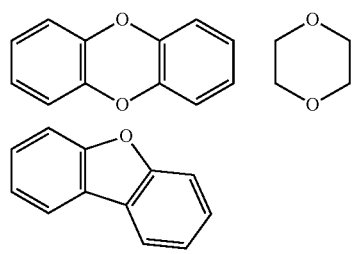

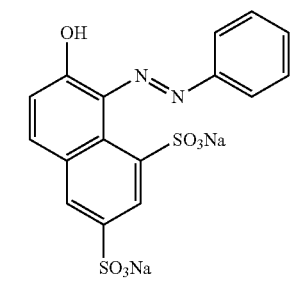

Orange G

| Reaction | Substrate | % remaining | Major product | % yield after 15 minutes |
|---|---|---|---|---|
| 1 | Dibenzodioxin | 62 | N/A | N/A |
| 2 | Dibenzofuran | 42 | Acetate | 58 |
| 3 | 1,4-dioxane | ~10 | Formate | 50 |

Many environmental pollutants are persistent in the environment or are difficult to treat due to their physical properties. The catalyst showed potential for further study in the remediation of environmental pollutants. The major products in two of the cases were benign acetate and formate.

Dye Bleaching Screen

Several different dyes were screened with the catalyst and $KHSO_5$ in water. The reaction was monitored by measuring the relative absorbance at $\lambda_{max}$ for each dye. A stock suspension of the catalyst (e.g., Co-dppe) was prepared in water. The suspension was thoroughly sonicated just prior to the experiment to ensure minimal aggregation. The stock dye and catalyst were added to a cuvette and the reaction was initiated by addition of stock $KHSO_5$ in water. Conditions: 40 µM dye, 1.5 mM oxidant, variable cat; RT open atm; 1 mL unbuffered H2O; monitor abs at λmax; Dyes Basic Blue 24, Brilliant Blue G, Bromophenol Blue, Buffalo Black, Methylene Green, Orange G. The structures of these dyes are shown below:

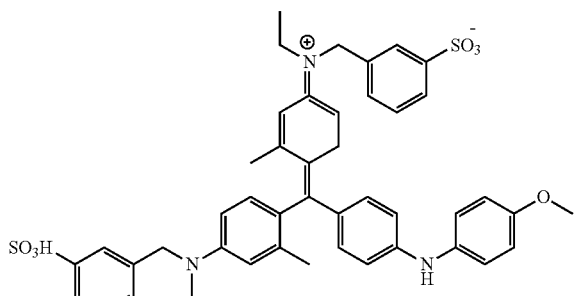

Brilliant Blue G

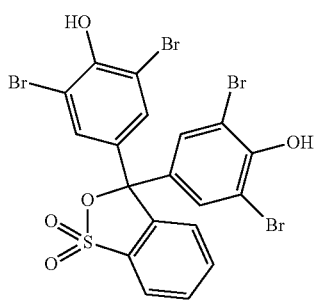

Bromophenol Blue

Figure 13:
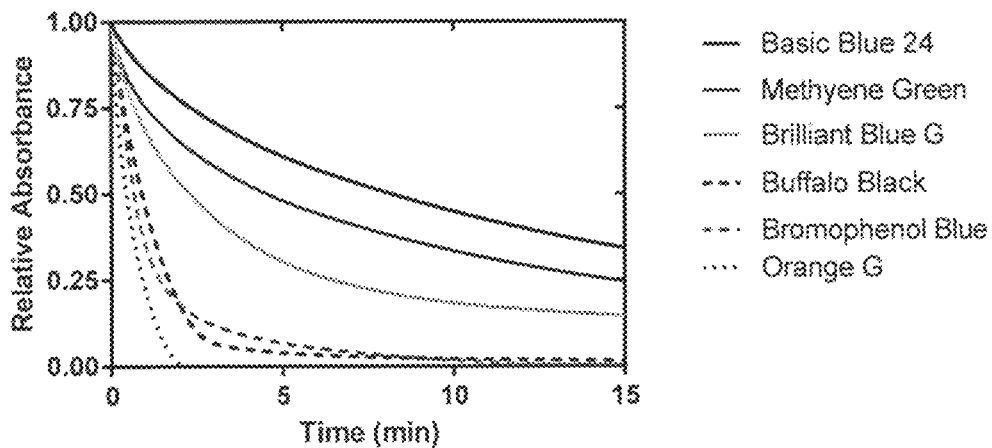
FIG. 13 is a graph showing the relative absorption for various times treated with catalyst as a function of time (minutes).

The results are shown in FIG. 13. The catalyst (e.g., Co-dppe) and KHSO$_5$ system was able to bleach a wide range of structurally different dyes. In most case reaching 50% of the initial absorbance in ca. 5 min.

Catalyst Dependence: Dye Bleaching

Figure 14:
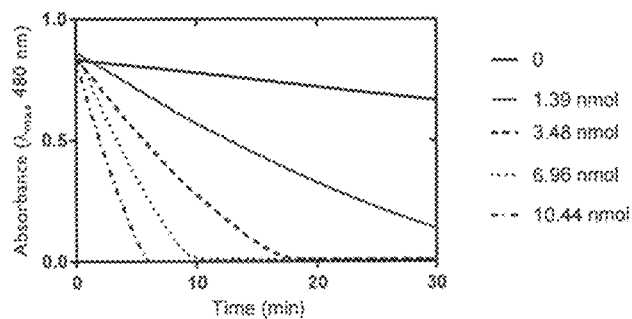
FIG. 14 is a graph showing the absorbance for Orange G dye as a function of catalyst concentration (nM) over time (minutes).

The series of reactions were set up identical to the above experiment. Orange G was chosen as the model dye and the loading of catalyst was varied (ca. 0, 1.4, 3.5, 7, 10.4 nmol). Conditions: 40 µM Orange G dye, 1.5 mM oxidant, variable cat; RT open atm; 1 mL unbuffered H$_2$O; monitor abs at λmax. The left over solution was centrifuged and decanted. To the decanted solution was added another aliquot of dye and oxidant. The results are shown in FIG. 14. The resulting rate was significantly slower than the initial rate but slightly faster than the rate of KHSO$_5$ alone. This suggests that soluble Co(II) species are not the primary catalyst for this reaction.

Figure 15:
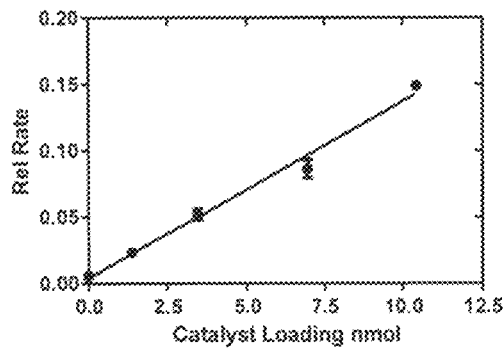
FIG. 15 is a graph showing the effect of catalyst loading on the rate of dye bleaching.

Despite the heterogenous nature of the catalyst the loading of the catalyst affects rate of dye bleaching. The results are shown in FIG. 15. The data shows that the catalyst is responsible for the rate of dye bleaching and not soluble Co(II) species.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims

We claim:

1. A method of oxidizing an organic compound comprising one or more carbon-hydrogen bonds, the method comprising contacting the organic compound to be oxidized with an oxidant selected from the group consisting of a chemical oxidant, an electrochemical oxidant, and combinations thereof and a catalyst having the chemical formula;

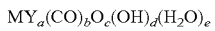

MY$_a$(CO)$_b$O$_c$(OH)$_d$(H$_2$O)$_e$ wherein

M is a d-block transition metal that forms stable carbonyl complexes selected from the group consisting of Cr, Mn, Co, Ni, Cu, Rh, Ir, and combinations thereof;

Y is a monodentate ligand, a bidentate ligand, or a combination thereof;

a is any value from 0.5 to 1;

b is any value from 0 to 3;

c is any value from 1 to 4; and d is any value from 0 to 4; and e is any value from 0 to 6, to oxidize a carbon-hydrogen bond in the organic compound; and wherein the catalyst is prepared according to a method comprising:

thermolysis of a solution comprising the d-block transition metal and the monodentate ligand, the bidentate ligand, or combinations thereof with stirring under reflux under an inert atmosphere;

allowing the resulting reaction mixture to cool followed by exposure to ambient atmosphere;

washing the reaction mixture; and drying the washed reaction mixture to obtain the catalyst.

2. The method of claim 1, wherein M is cobalt.
3. The method of claim 1, wherein M is nickel.
4. The method of claim 1, wherein the M is chromium.
5. The method of claim 1, wherein the M is copper.
6. The method of claim 1, wherein the M is manganese.
7. The method of claim 1, wherein the M is rhodium.
8. The method of claim 1, wherein the M is iridium.
9. The method of claim 1, wherein b is from 0 to 2.
10. The method of claim 1, wherein c is from 1.5 to 3.
11. The method of claim 1, wherein Y is charged.
12. The method of claim 1, wherein Y is uncharged.
13. The method of claim 12, wherein Y is a phosphorus ligand.
14. The method of claim 13, wherein the phosphorus ligand is selected from the group consisting of dialkyl phosphines, trialkyl phosphine, alkyl diaryl phosphines, triaryl phosphines, and combinations thereof.
15. The method of claim 14, wherein the phosphorus ligand is an alkyl diaryl phosphine.
16. The method of claim 15, wherein the alkyl diaryl phosphine is selected from the group consisting of 1,2-Bis(diphenylphosphino)ethane, 4,5-Bis(diphenylphosphino)-9,9-dimethylxanthene, triphenylphosphine, (Oxydi-2,1-phenylene)bis(diphenylphosphine), and combinations thereof.
17. The method of claim 12, wherein the ligand is a nitrogen ligand.
18. The method of claim 17, wherein the nitrogen ligand is a N-heterocycle.
19. The method of claim 18, wherein the N-heterocycle is selected from the group consisting of 2,2'-bipyridine, 3,3'-bipyridine, and combinations thereof.
20. The method of claim 12, wherein the nitrogen ligand is a secondary amine, tertiary amine, or combinations thereof.
21. The method of claim 20, wherein the secondary amine, tertiary amine, or combinations thereof are substituted with alkyl and/or aryl groups.
22. The method of claim 1, wherein the ligand is a sulfur ligand.
23. The method of claim 22, wherein the sulfur ligand is selected from the group consisting of S-heterocycles, alkyl and/or aryl thioethers, or combinations thereof.
24. The method of claim 12, wherein the ligand is an arsenic ligand.
25. The method of claim 24, wherein the arsenic ligand is selected from the group consisting of As-heterocycles, tertiary arsine with alkyl and/or aryl substituents, and combinations thereof.
26. The method of claim 1, wherein the oxidant is a chemical oxidant.
27. The method of claim 26, wherein the chemical oxidant is selected from the group consisting of potassium hydrogen peroxysulfate, hydrogen peroxide, oxygen, ozone, and combinations thereof.
28. The method of claim 1, wherein the oxidant is an electrochemical oxidant.
29. The method of claim 1, wherein the oxidant comprises a combination of a chemical oxidant and an electrochemical oxidant.
30. The method of claim 1, wherein Y is a bidentate ligand.

* * * * *